US008147515B2

(12) United States Patent
Ohdaira

(10) Patent No.: US 8,147,515 B2
(45) Date of Patent: Apr. 3, 2012

(54) MEDICAL HOLDING APPARATUS AND METHOD OF USING MEDICAL HOLDING APPARATUS

(75) Inventor: Takeshi Ohdaira, Shimotsuke (JP)

(73) Assignee: Jichi Medical University, Shimotsuke-shi, Tochigi (JP)

( * ) Notice: Subject to any disclaimer, the term of this patent is extended or adjusted under 35 U.S.C. 154(b) by 605 days.

(21) Appl. No.: 12/306,932

(22) PCT Filed: Jun. 29, 2007

(86) PCT No.: PCT/JP2007/063091
§ 371 (c)(1),
(2), (4) Date: Dec. 29, 2008

(87) PCT Pub. No.: WO2008/001882
PCT Pub. Date: Jan. 3, 2008

(65) Prior Publication Data
US 2009/0306686 A1 Dec. 10, 2009

(30) Foreign Application Priority Data

Jun. 30, 2006 (JP) ................................. 2006-182647

(51) Int. Cl.
*A61B 17/04* (2006.01)
*A61B 17/08* (2006.01)
(52) U.S. Cl. ........................................ 606/232; 606/151
(58) Field of Classification Search .................... 606/74, 606/103, 113, 151, 153, 213, 215, 219, 232, 606/233; 600/12, 29, 30
See application file for complete search history.

(56) References Cited

U.S. PATENT DOCUMENTS

| 4,154,226 A | * | 5/1979 | Hennig et al. ................... 600/30 |
| 5,021,059 A | * | 6/1991 | Kensey et al. ................. 606/232 |
| 6,027,523 A | * | 2/2000 | Schmieding ................... 606/232 |

FOREIGN PATENT DOCUMENTS

| JP | 2005-028006 A | 2/2005 |
| JP | 2005-103107 A | 4/2005 |

* cited by examiner

*Primary Examiner* — Julian Woo
(74) *Attorney, Agent, or Firm* — McLeland Patent Law Office, P.L.L.C.

(57) ABSTRACT

A medical holding apparatus provided with an anchor member composed of a tying-up portion to be tied up to an intracorporeal tissue and a first connection portion; and a locking member composed of a holding portion for holding another intracorporeal tissue, a medical instrument or a drug and a second connection portion, in which the first connection portion and the second connection portion can be detachably connected to each other. A method of using the medical holding apparatus comprising steps of inserting the anchor member into a lumen of a cylindrical member; bringing the cylindrical member distal end close to a predetermined intracorporeal tissue surface; pushing the anchor member from the cylindrical member proximal end side so as to project the anchor member out of the cylindrical member distal end and tying up the anchor member to the intracorporeal tissue; holding another intracorporeal tissue, the medical instrument or the drug by the holding portion of the locking member; and connecting the second connection portion to the first connection portion by a magnetic force and the like.

23 Claims, 17 Drawing Sheets

[Fig. 1]
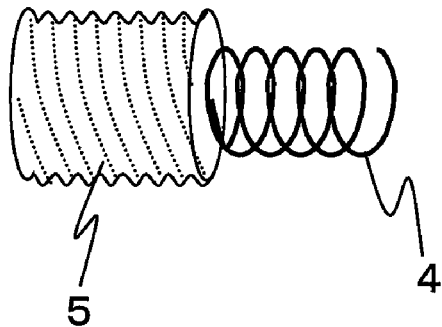
[Fig. 2]
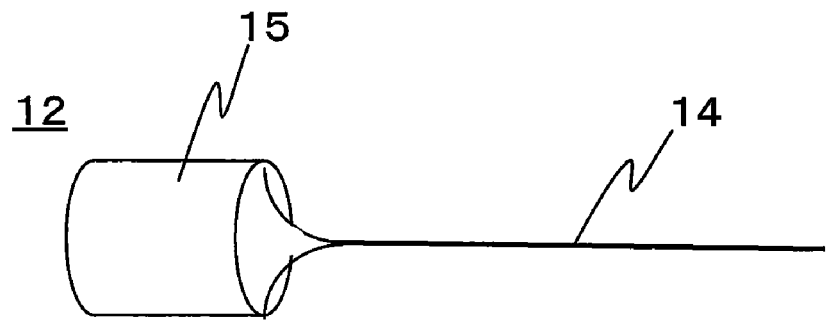
[Fig. 3]
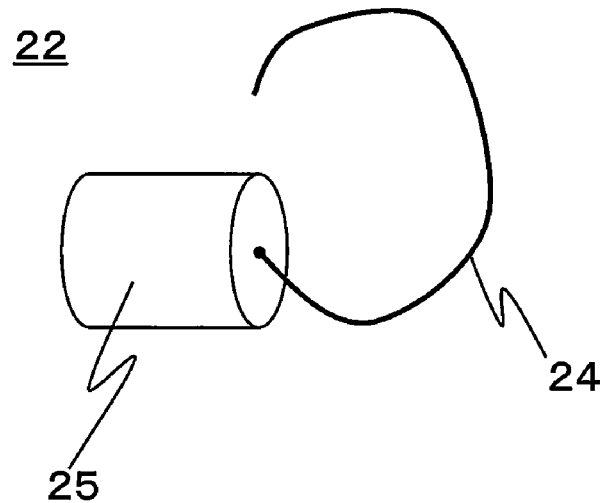

[Fig. 4]
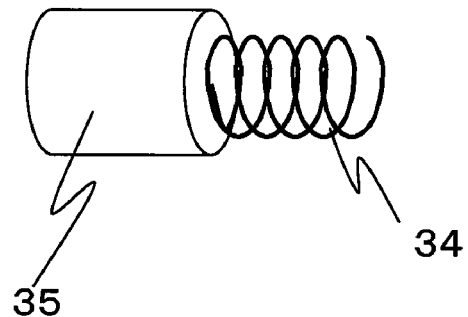
[Fig. 5]
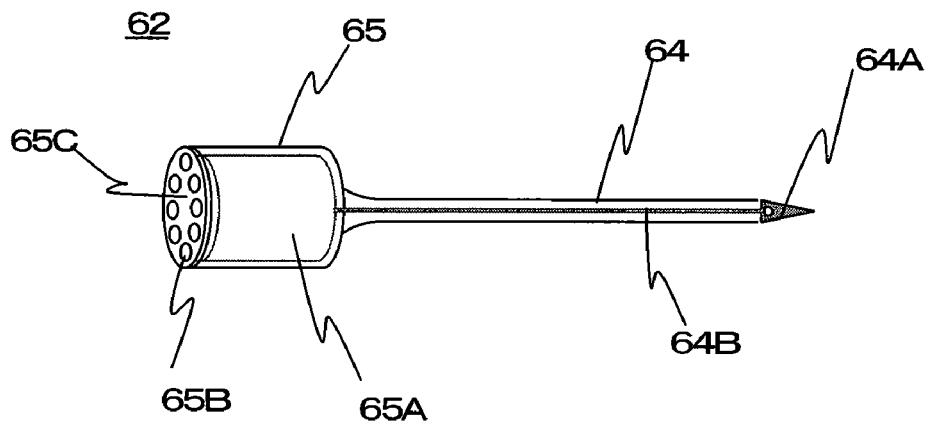
[Fig. 6]
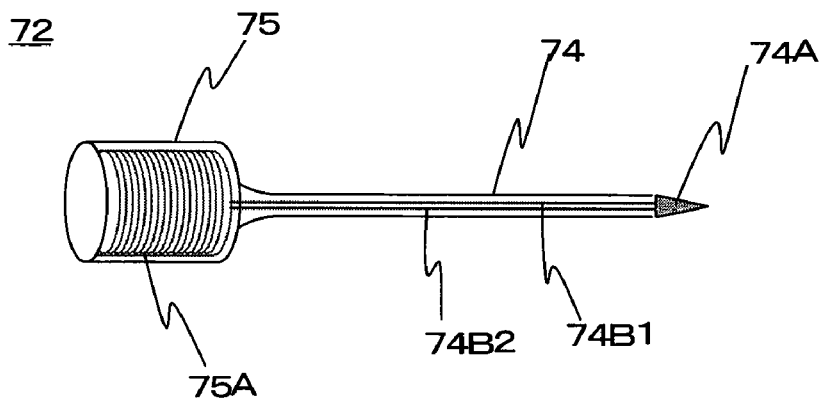

[Fig. 7]
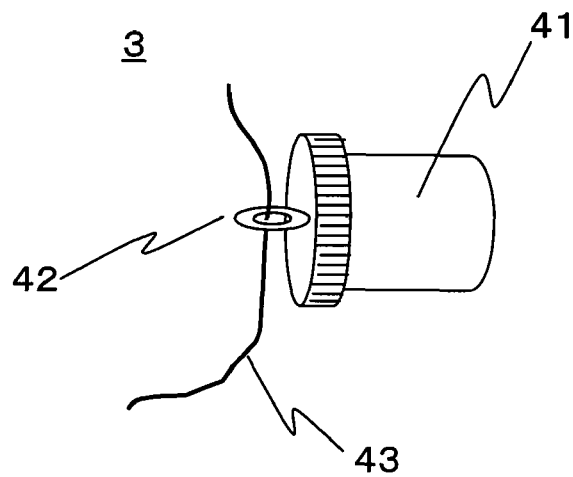
[Fig. 8]
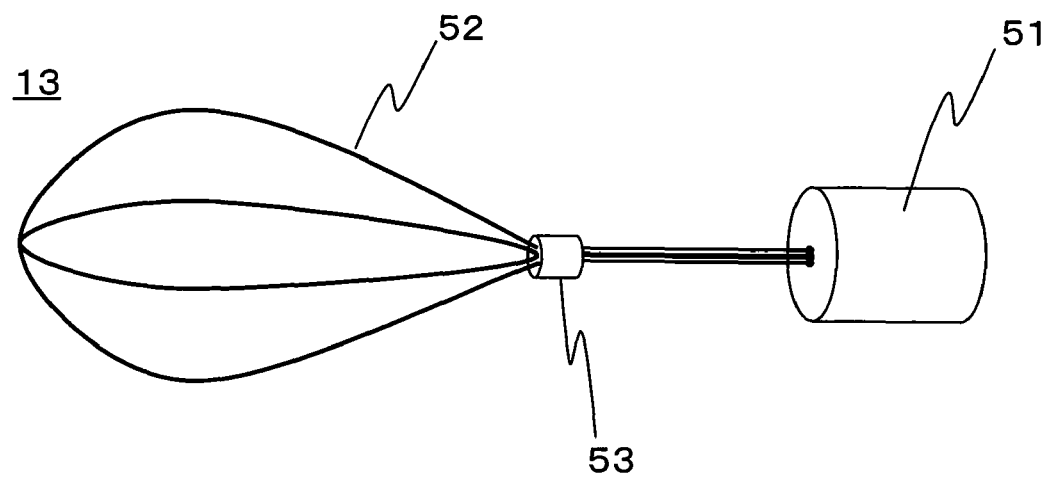

[Fig. 9]
23a
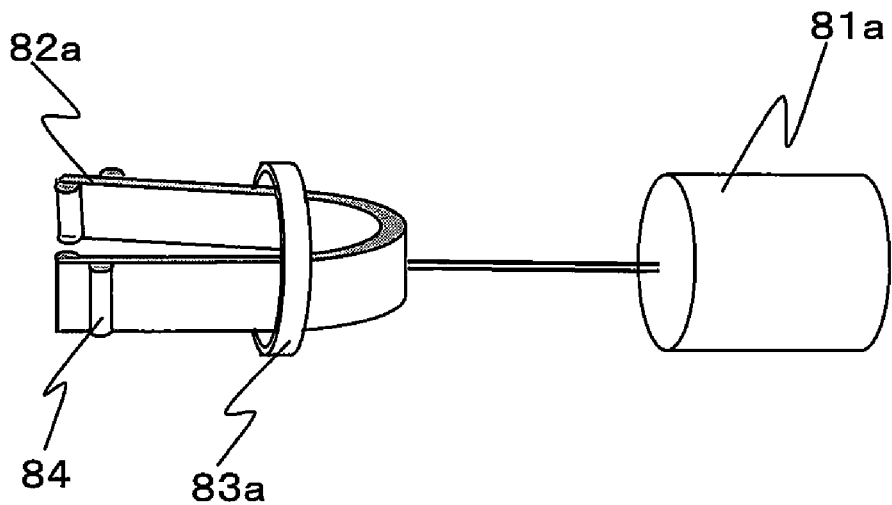
(a)
23b
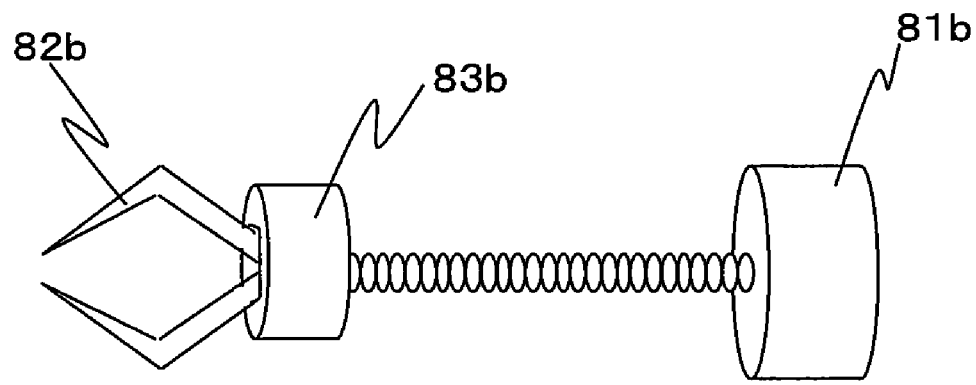
(b)

[Fig. 10]
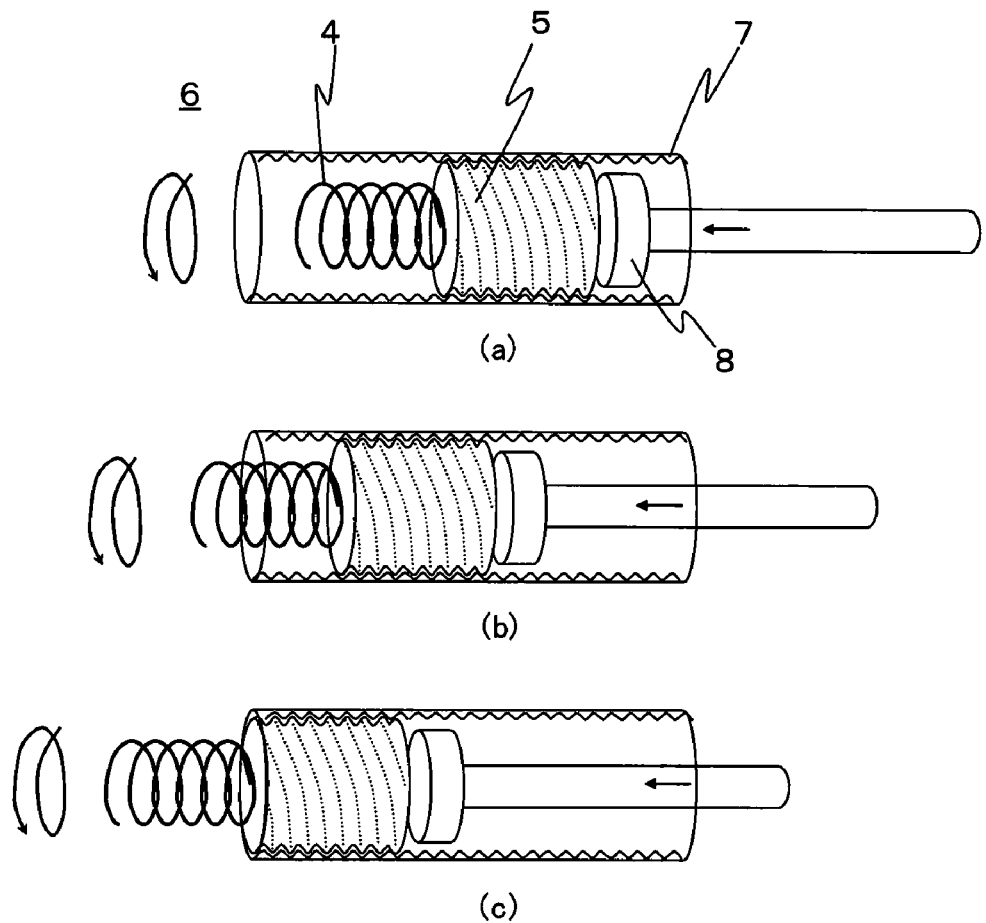
[Fig. 11]
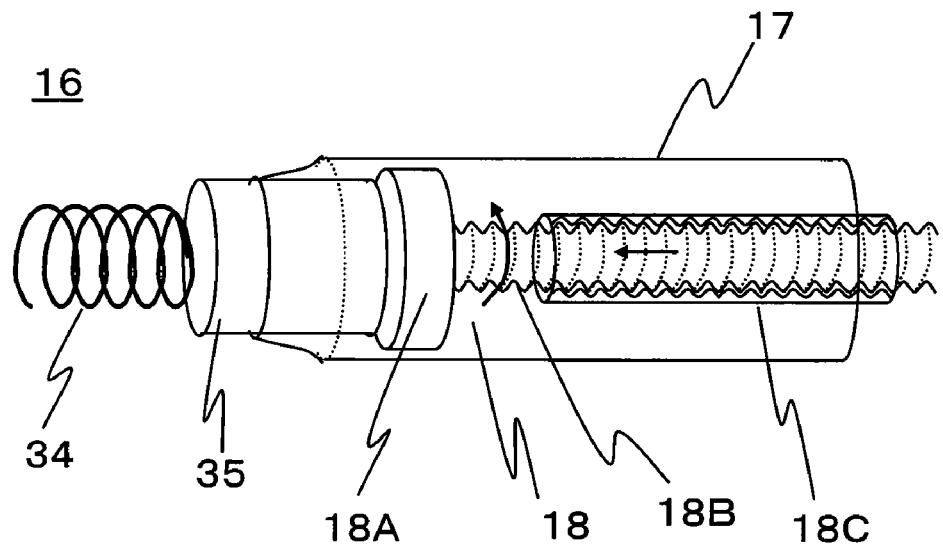

[Fig. 12]
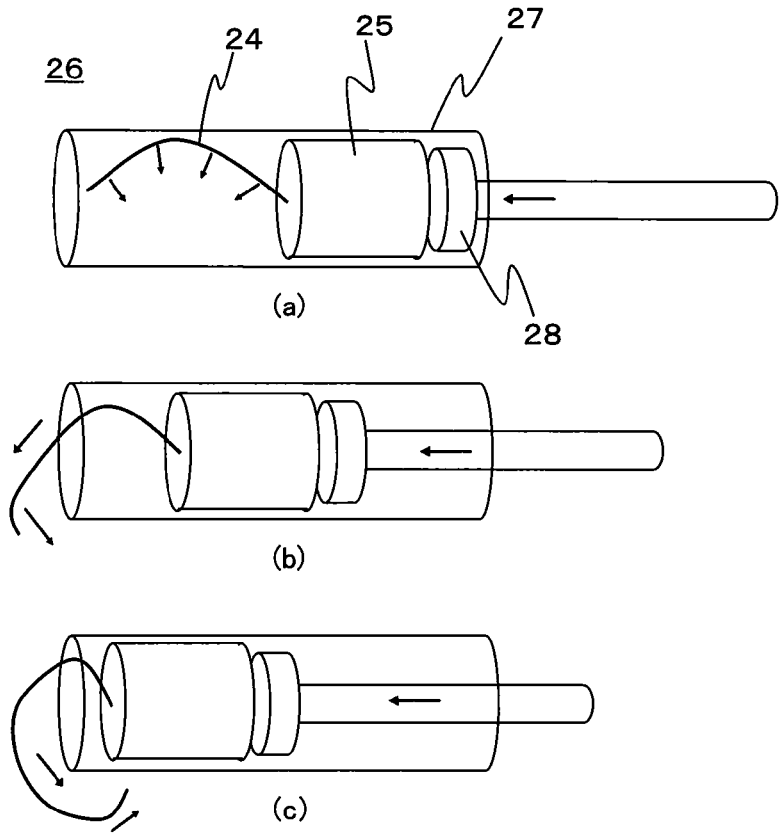
[Fig. 13]
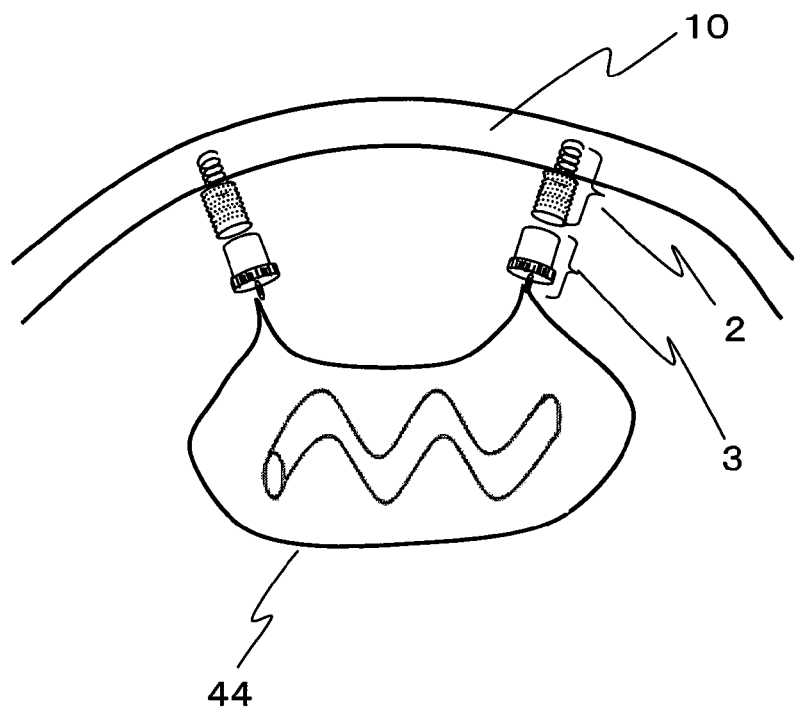

[Fig. 14]
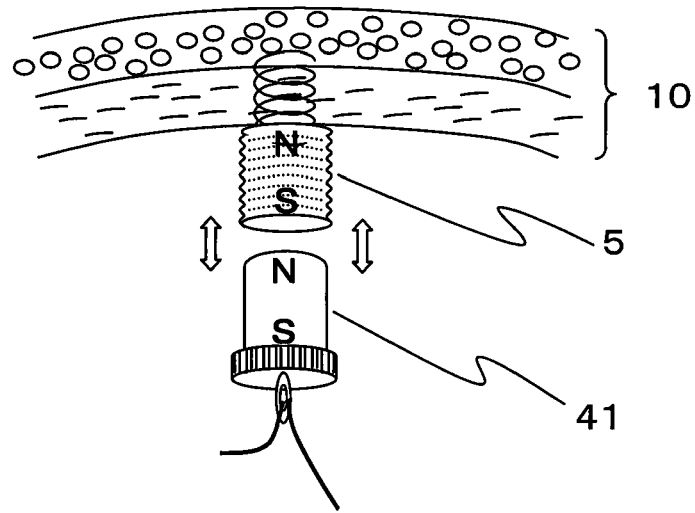
[Fig. 15]
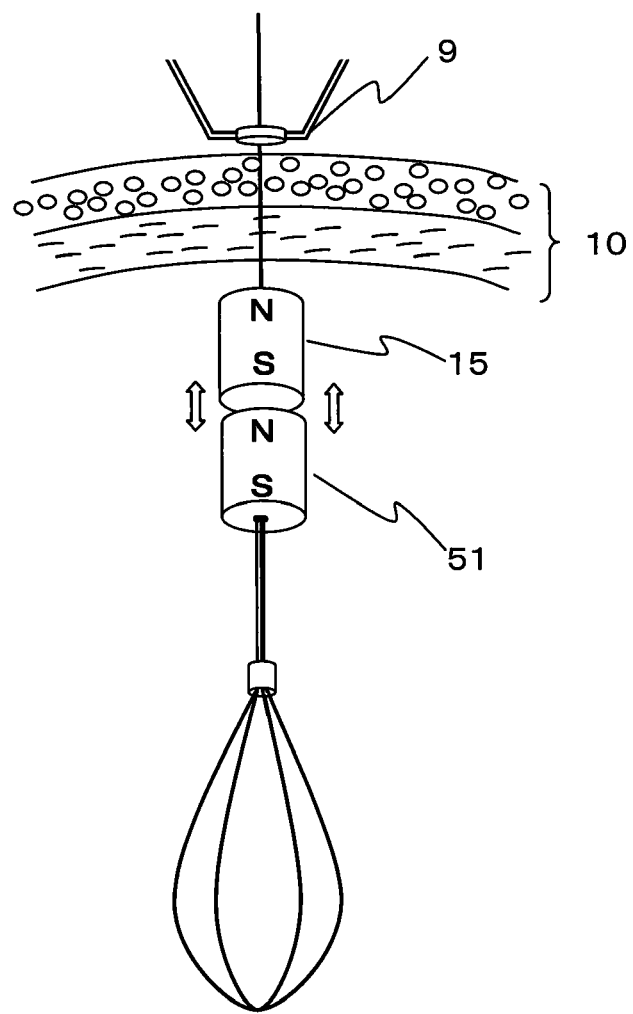

[Fig. 16]
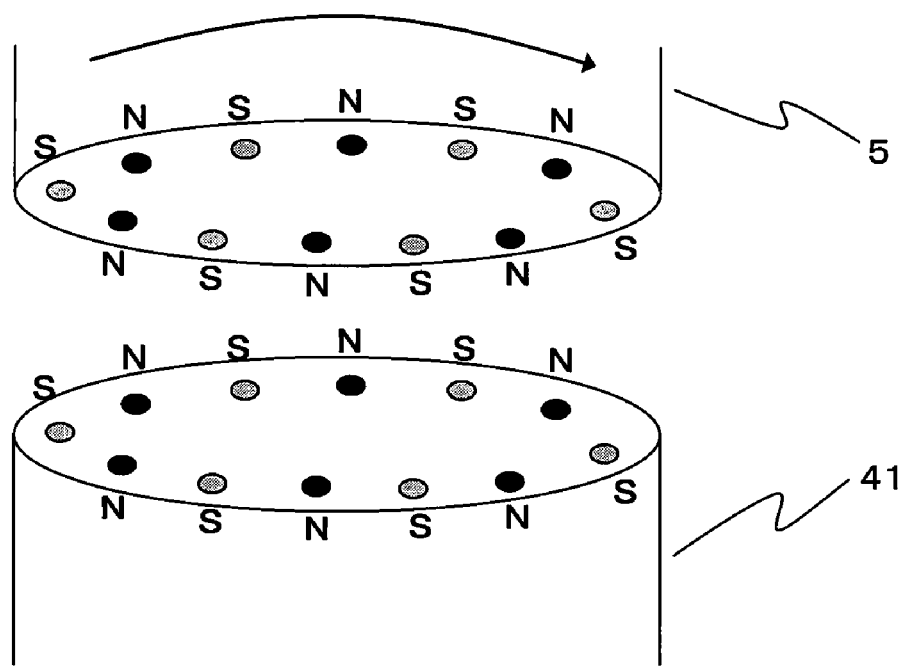
[Fig. 17]
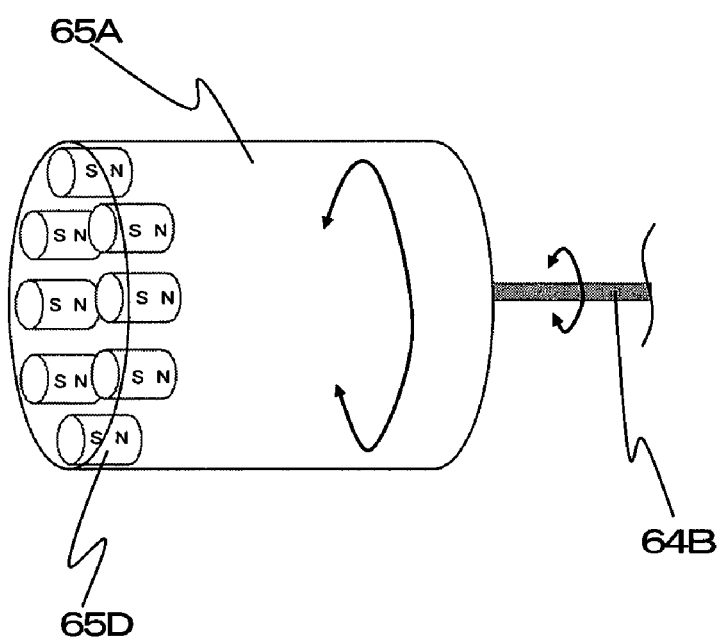

[Fig. 18]
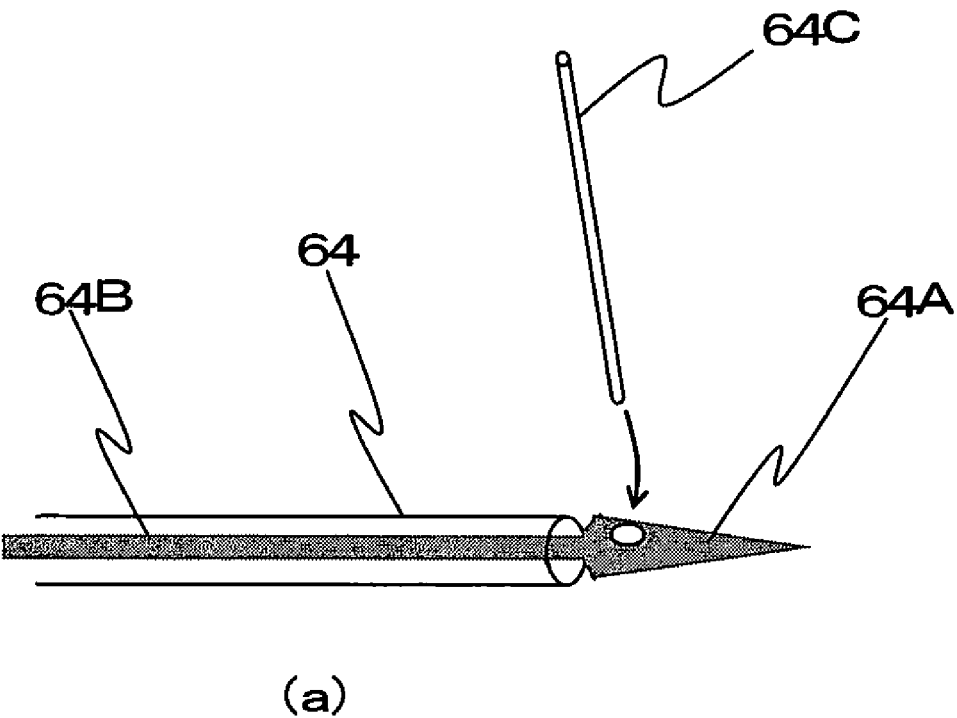
(a)
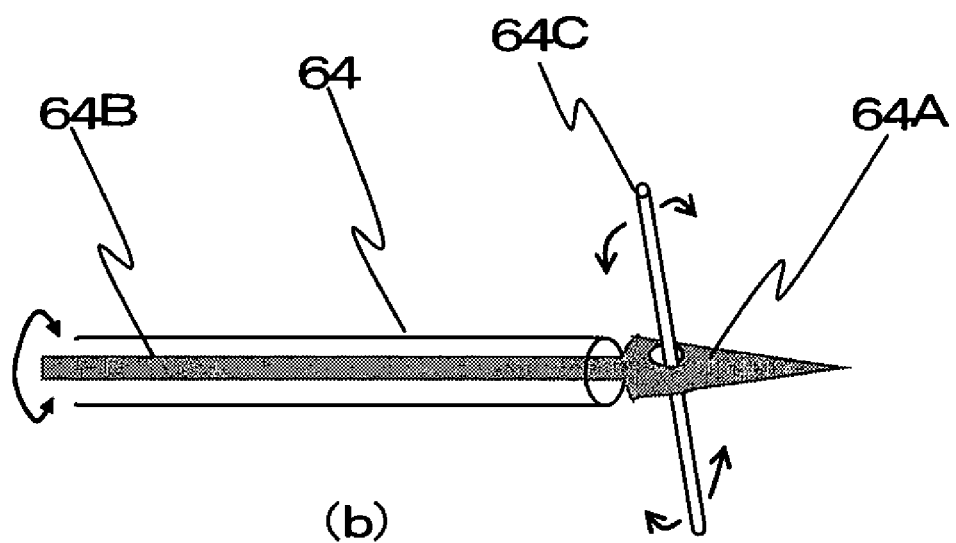
(b)

[Fig. 19]
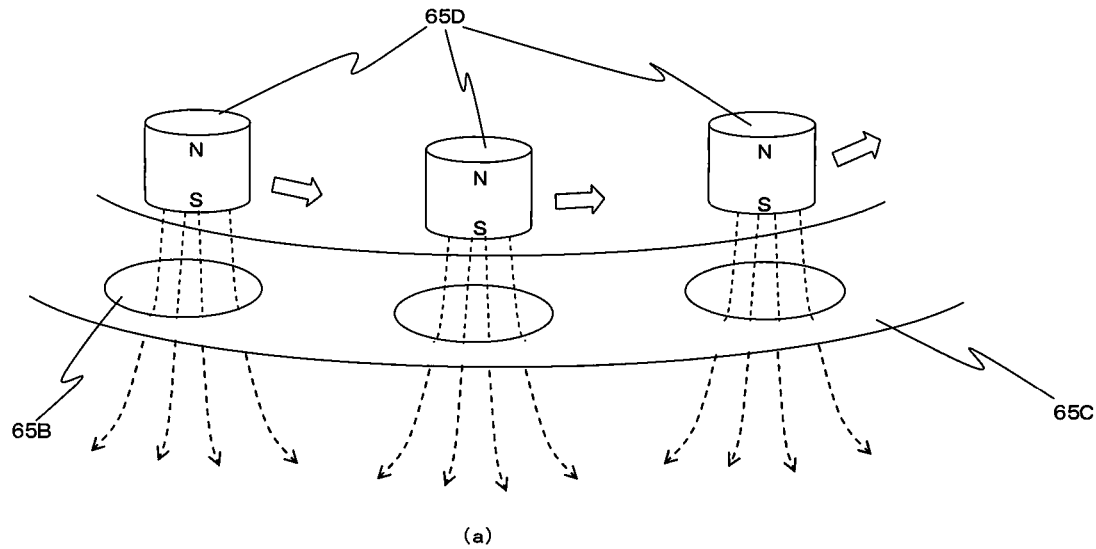
(a)
(b)
[Fig. 20]
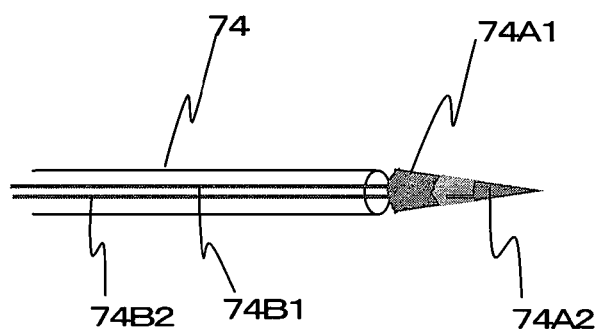

[Fig. 21]
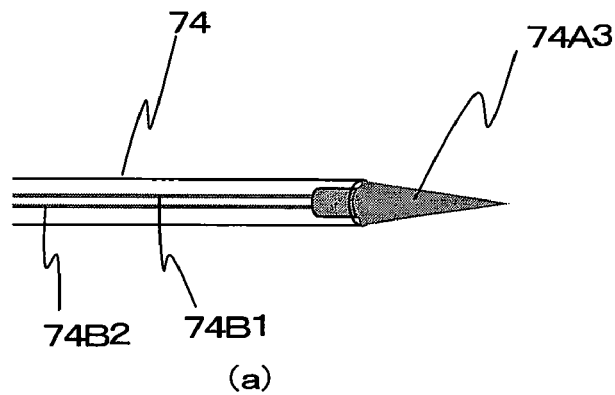
(a)
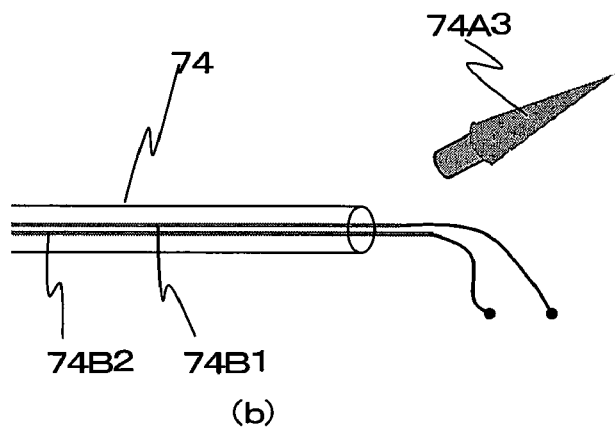
(b)
[Fig. 22]
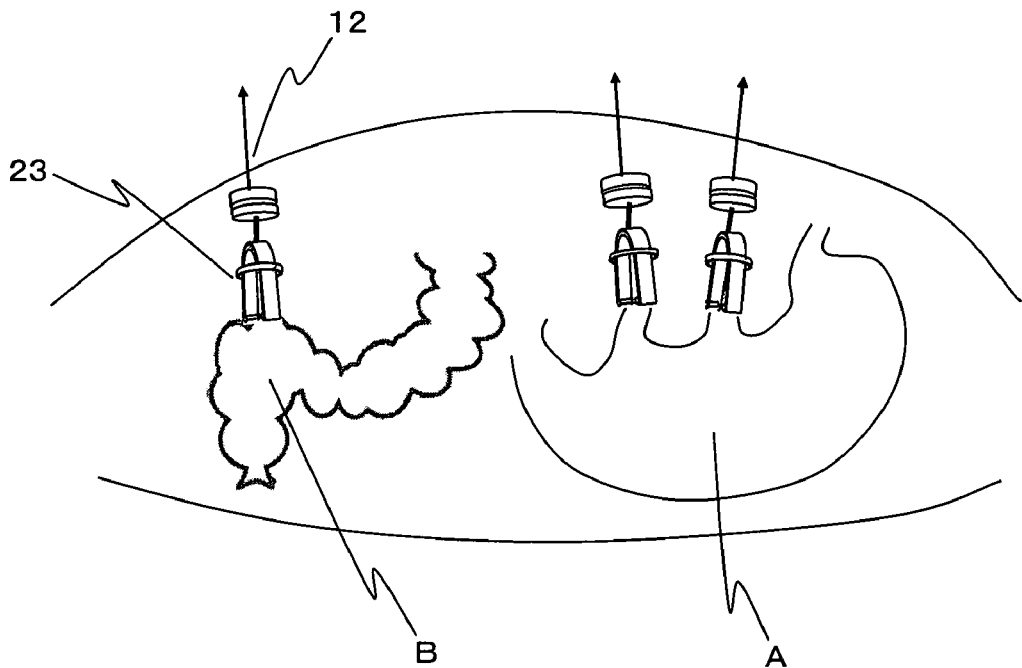

[Fig. 23]
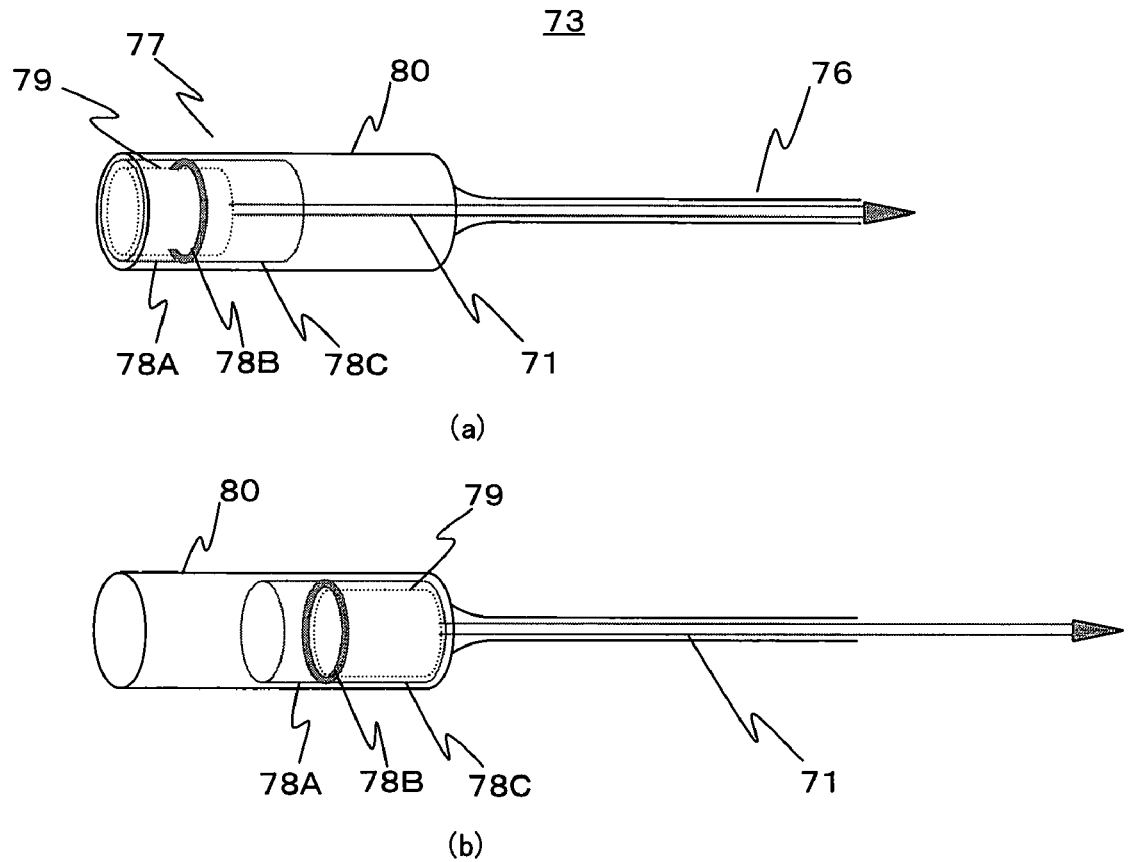
(a)
(b)
[Fig. 24]
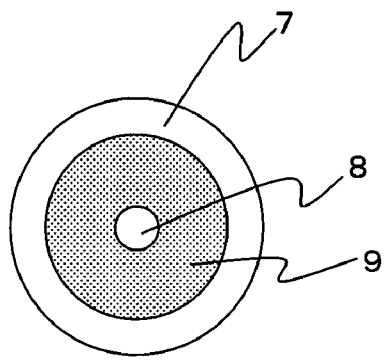

[Fig. 25]
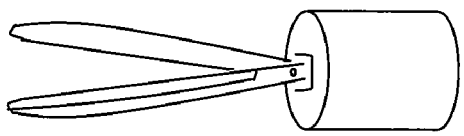
(a)
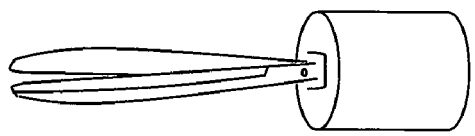
(b)
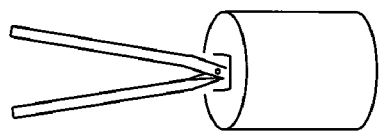
(c)
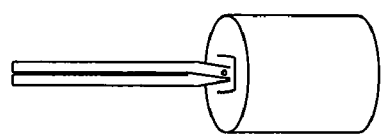
(d)
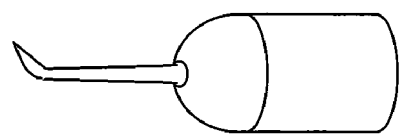
(e)
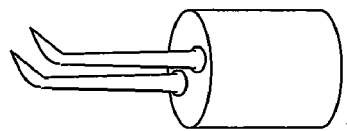
(f)
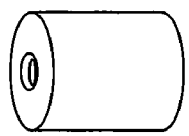
(g)
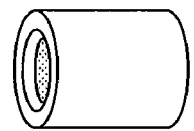
(h)

[Fig. 26]
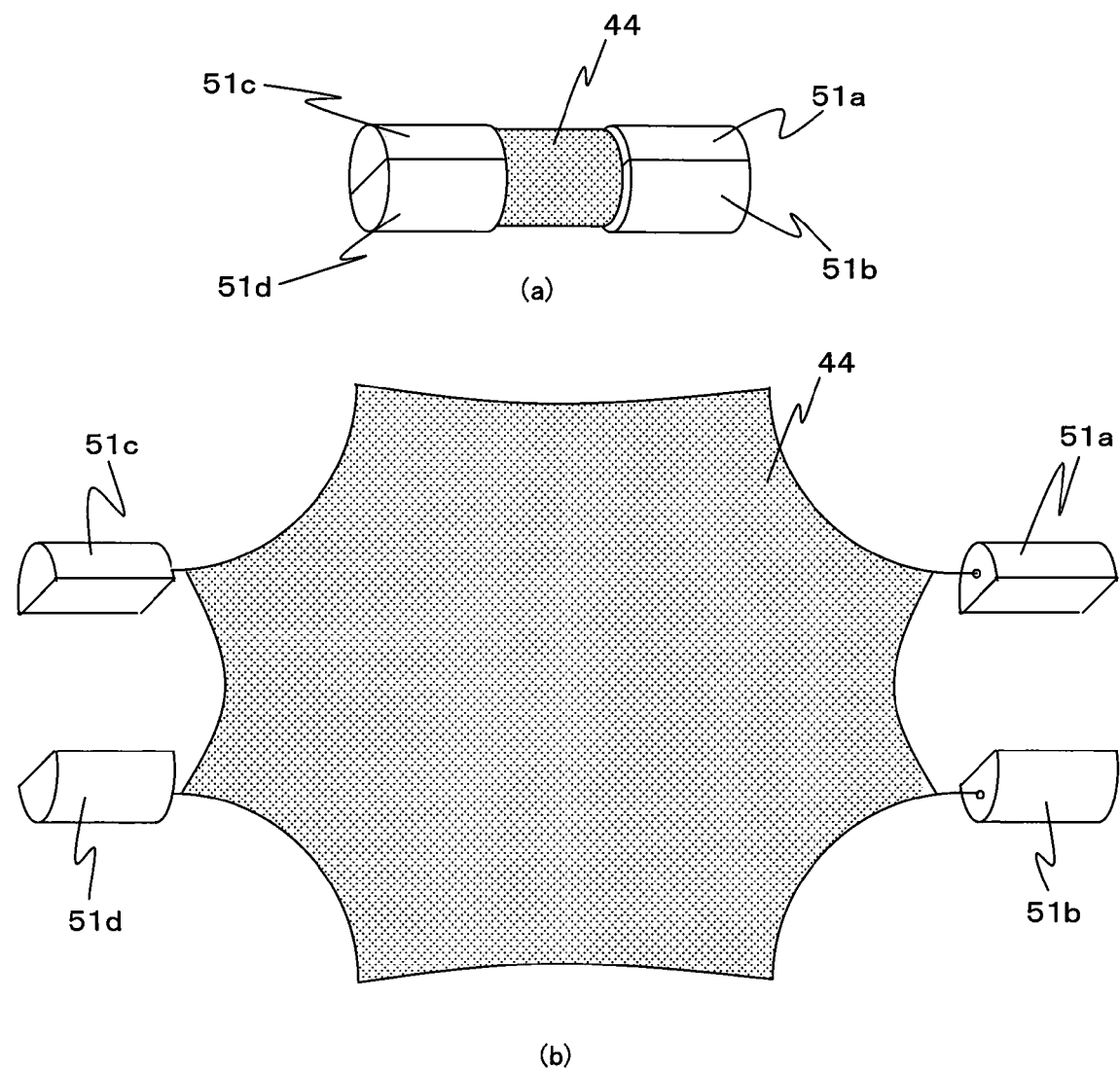

[Fig.27]
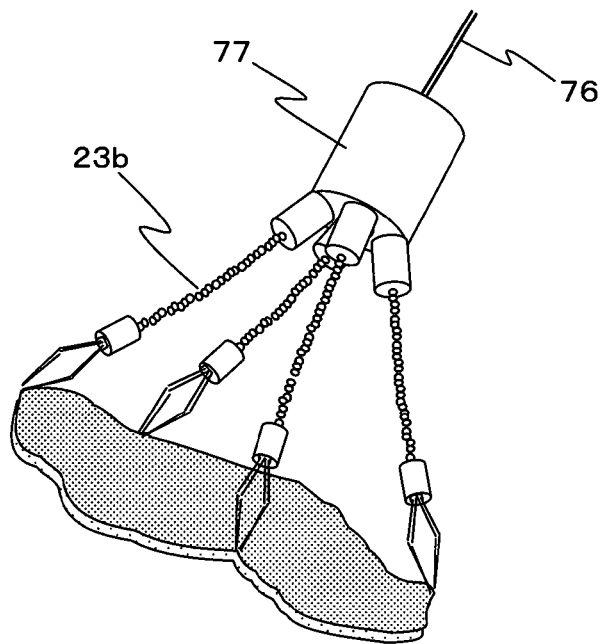
[Fig. 28]
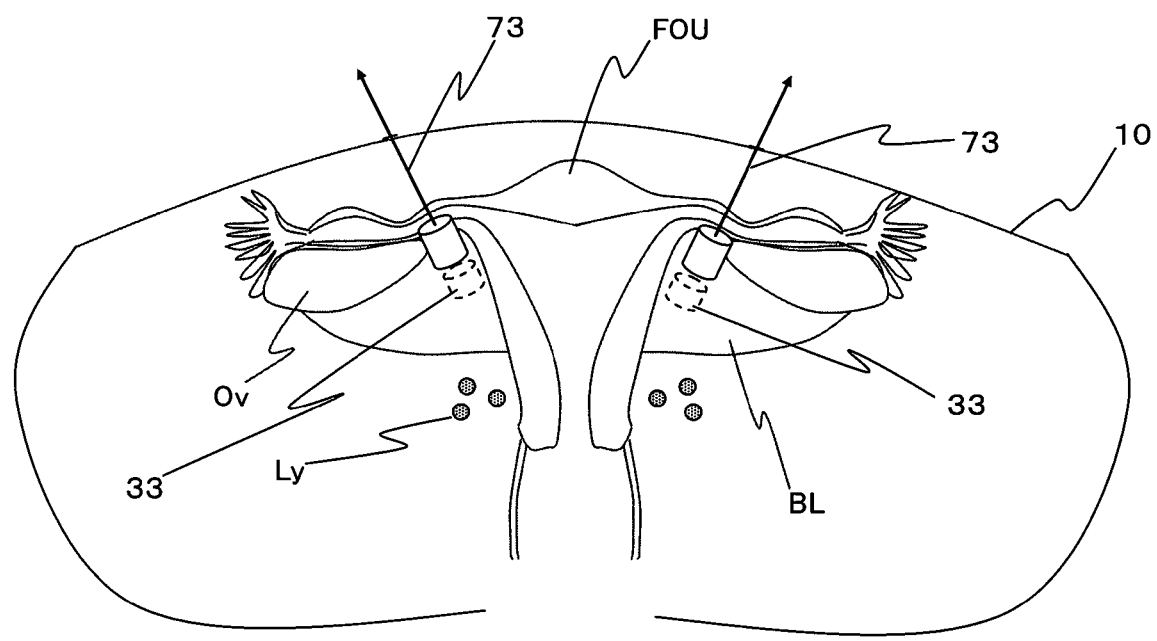

[Fig. 29]
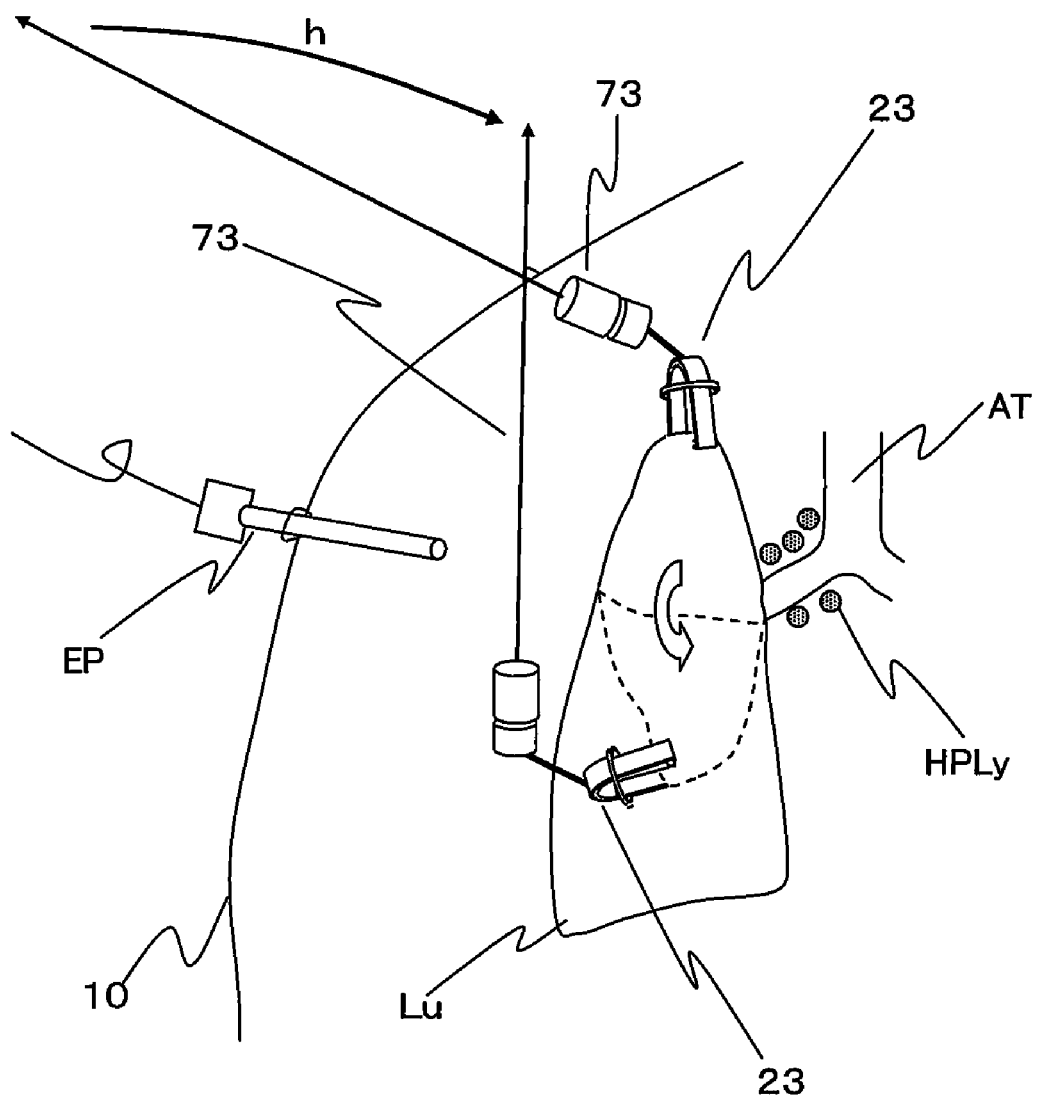

[Fig. 30]
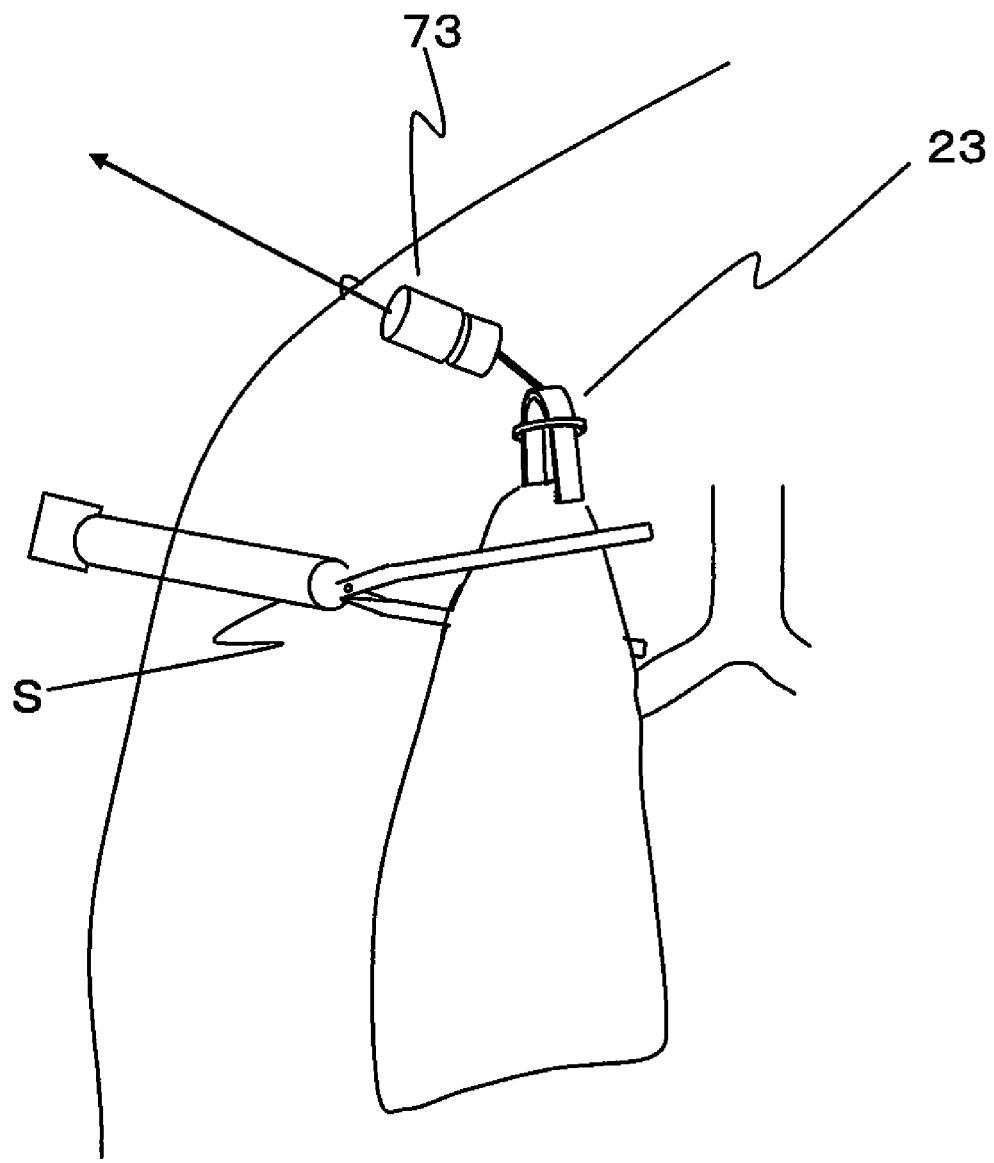

MEDICAL HOLDING APPARATUS AND METHOD OF USING MEDICAL HOLDING APPARATUS

TECHNICAL FIELD

The present invention relates to a medical holding apparatus, an anchor-member tying-up assisting tool and the tying-up method for tying the medical holding apparatus to an intracorporeal tissue easily, and a method of using the medical holding apparatus. In more detail, in an abdominal cavity surgery or chest cavity surgery using an endoscope, a medical holding apparatus that can easily hold an intracorporeal tissue other than the intracorporeal tissue to be treated, a medical instrument or a drug in an abdominal cavity or chest cavity, a tying-up assisting tool and the tying-up method for easily tying up the medical holding apparatus to a desired spot in an intracorporeal tissue such as an abdominal wall or chest wall, and a method of using the medical holding apparatus for easily holding the intracorporeal tissue other than the intracorporeal tissue to be treated in an abdominal cavity or chest cavity, a medical instrument or a drug in an abdominal cavity or chest cavity.

BACKGROUND ART

A laparoscopic surgery or thoracoscopic surgery is a method (hereinafter referred to as endoscopic surgery in some cases), of which a state in an abdominal cavity or chest cavity is reproduced on a video screen through a laparoscope or thoracoscope without opening the abdominal cavity, and the surgery is carried out using a special instrument while the screen is watched. In an endoscopic surgery, the surgery is carried out only by opening a plurality of small holes of approximately 5 to 10 mm in the abdomen or chest. In the laparoscopic surgery or thoracoscopic surgery, since wounds are small as above, pain after the surgery is less and since the wounds become substantially invisible, it has an esthetic merit. Also, duration of hospitalization can be short and rehabilitation into society is early. Under these circumstances, "NOTES (Natural Orifice Transluminal Endoscopic Surgery)" has drawn attention, and application to some diseases have been tried. According to the NOTES, a small hole is opened in a vaginal wall, intestinal wall, esophagus wall, gastric wall and the like through a vagina, rectum or mouth, an endoscope is inserted into a body cavity through the hole and an affected part in the body cavity can be treated through a vagina, rectum or mouth, for example. This surgery is expected to lead to alleviation of pain and cicatrix and drastic reduction of time required for recovery since ablation on the body surface can be minimized or eliminated.

However, in such endoscopic surgeries, a field of view of the endoscope is small and moreover, an intracorporeal tissue other than a treatment target interrupts the field of view of the endoscope and a treatment site, which might obstruct the treatment and incur prolongation of the entire operation time. Methods to prevent such interruption of the field of view or treatment site have been proposed.

For example, Patent Document 1 discloses a medical grasping tool that grasps an intracorporeal tissue such as mucosa at endoscopic demucosation and the like. This medical grasping tool is provided with a pair of grasping members for grasping an intracorporeal tissue and a connecting member for connecting the pair of grasping members. As grasping means, a clip provided with opposing claws, a ring or elastic band capable of reducing an opening diameter and tying the intracorporeal tissue, a sucker for sucking the organ or tissue by a negative pressure, a mesh bag or basket that can wrap an organ or tissue, a needle provided with a mechanism that is pierced into the intracorporeal tissue and prevents removal after that and the like are exemplified.

Patent Document 1: Japanese Patent Laid-Open No. 2005-103107

However, this medical grasping tool is used for holding a relatively light-weight target such as an ablated mucosa and the like and not intended to be used for holding an intracorporeal tissue such as a digestive tract that is relatively heavy and easily moves in an abdominal cavity or chest cavity. Also, since the grasping members are fixed to both ends of the connecting member, if the grasping tool is to be re-mounted at another spot or a different type of grasping means is required, the both ends of the medical grasping tool grasping the intracorporeal tissue should be removed and have to grasp the intracorporeal tissue again.

DISCLOSURE OF THE INVENTION

Problems to be Solved by the Invention

The present invention has an object to provide, in a laparoscopic surgery or thoracoscopic surgery using an endoscope, a medical holding apparatus that can hold an intracorporeal tissue other than an intracorporeal tissue to be treated, a medical instrument or a drug in a body cavity, a tying-up assisting tool and a method of tying-up for easily tying up the medical holding apparatus at a desired spot in the intracorporeal tissue such as an abdominal wall or chest wall, and a method of using the medical holding apparatus for easily holding the intracorporeal tissue other than the intracorporeal tissue to be treated in the body cavity, the medical instrument or the drug in the body cavity.

Means for Solving the Problems

After a keen examination in order to solve the above problems, the inventor reached an idea to separate two grasping members at both ends for grasping an intracorporeal tissue and the like and to connect the separated grasping means by a detachable connecting member. And thereby the inventor found out that the intracorporeal tissue other than the intracorporeal tissue to be treated in a body cavity, a medical instrument or a drug can be easily held in the body cavity. The present invention has been completed as the result of further examination based on these findings.

That is, the present invention is as follows:

(1) A medical holding apparatus, comprising an anchor member having a tying-up portion to be tied up to an intracorporeal tissue and a first connection portion; and a locking member having a second connection portion, in which the first connection portion and the second connection portion can be detachably connected to each other directly or with another intracorporeal tissue between the first connection portion and the second connection portion.

(2) A medical holding apparatus, comprising an anchor member having a tying-up portion to be tied up to an intracorporeal tissue and a first connection portion; and a locking member having a medical operation portion and a second connection portion, in which the first connection portion and the second connection portion can be detachably connected.

(3) The medical holding apparatus described in (2), in which the medical operation portion includes at least one medical instrument selected from the group consisting of an image pickup device, an illumination element, forceps, scissors, a scalpel, a snare, and laser.

(4) A medical holding apparatus, comprising an anchor member having a tying-up portion to be tied up to an intracorporeal tissue and a first connection portion; and a locking member having a holding portion for holding another intracorporeal tissue, a medical instrument or a drug and a second connection portion, in which the first connection portion and the second connection portion can be detachably connected.

(5) The medical holding apparatus described in (4), in which the holding portion has a bag, a basket, a thread, a wire or a clip that can hold another intracorporeal tissue.

(6) The medical holding apparatus described in any one of (1) to (5), in which the tying-up portion has a spiral, hook-like or straight puncture needle that can be tied up by puncturing an intracorporeal tissue.

(7) The medical holding apparatus described in any one of (1) to (5), in which the tying-up portion has a straight puncture needle that can be tied up by penetrating an intracorporeal tissue, and a latching means for restraining the straight puncture needle penetrating the intracorporeal tissue so that the first connection portion is positioned at a predetermined position is further comprised.

(8) The medical holding apparatus described in any one of (1) to (7), in which the first connection portion and/or the second connection portion is made of a paramagnetic substance or a ferromagnetic substance, and at least any one of the first connection portion and/or the second connection portion is a magnet.

(9) The medical holding apparatus described in any one of (1) to (8), in which the anchor member and/or the locking member is covered by a biocompatible material.

(10) A medical anchor member comprising a tying-up portion to be tied up at an intracorporeal tissue and a first connection portion.

(11) A medical anchor member, in which a tying-up portion has a straight puncture needle that can be tied up by penetrating an intracorporeal tissue and a latching means for restraining the straight puncture needle penetrating the intracorporeal tissue so that the first connection portion is positioned at a predetermined position is further comprised.

(12) The medical anchor member described in (11), in which the first connection portion has a cavity inside, the tying-up portion is cylindrical, the cavity of the first connection portion and an in-cylinder lumen of the tying-up portion communicate with each other; a magnet movable in the longitudinal direction is provided in the cavity of the first connection portion; a rod-like body penetrating the in-cylinder lumen of the tying-up portion and movable in the longitudinal direction is linked at a proximal end of the magnet, and the rod-like body and the magnet are made movable in the longitudinal direction in an interlocking manner.

(13) A medical locking member comprising a holding portion for holding another intracorporeal tissue, a medical instrument or a drug and a second connection portion.

(14) A medical locking member comprising a medical operation portion and a second connection portion.

(15) An anchor-member tying-up assisting tool, comprising a cylindrical member having a lumen into which an anchor member having a tying-up portion to be tied up to an intracorporeal tissue and a first connection portion can be inserted so that the tying-up portion is oriented to a distal end side and the first connection portion to a proximal end side; and a pushing-out member for projecting the anchor member out of the cylindrical member distal end by pushing the inserted anchor member from the cylindrical member proximal end side.

(16) A method of tying-up an anchor member to an intracorporeal tissue, comprising steps of:
inserting the anchor member having a tying-up portion to be tied up to an intracorporeal tissue and a first connection portion into a lumen of a cylindrical member so that the tying-up portion is oriented to a distal end side and the first connection portion to a proximal end side;
bringing the cylindrical member distal end close to a predetermined intracorporeal tissue surface; and
pushing the anchor member from the cylindrical member proximal end side so as to project the anchor member out of the cylindrical member distal end.

(17) The method of using the medical holding apparatus described in any one of (1) to (9), in which the anchor member is tied up to the intracorporeal tissue, and the first connection portion of the anchor member is connected to the second connection portion of the locking member.

(18) The method of using the medical holding apparatus described in any one of (1) to (9), in which the anchor member is tied up to the intracorporeal tissue, and the first connection portion is connected to the second connection portion so that another intracorporeal tissue is sandwiched between the first connection portion of the anchor member and the second connection of the locking member.

(19) The method of using the medical holding apparatus described in any one of (1) to (9), comprising steps of:
inserting the anchor member having the tying-up portion to be tied up to an intracorporeal tissue and the first connection portion into a lumen of a cylindrical member so that the tying-up portion is oriented to a distal end side and the first connection portion to a proximal end side;
bringing the cylindrical member distal end close to a predetermined intracorporeal tissue surface;
pushing the anchor member from the cylindrical member proximal end side so as to project the anchor member out of the cylindrical member distal end and to tie up the anchor member to the intracorporeal tissue; and
connecting the second connection portion of the locking member to the first connection portion of the anchor member.

Advantages of the Invention

In the medical holding apparatus according to the present invention, the anchor member to be tied up to an intracorporeal tissue such as an abdominal wall or chest wall and the locking member for holding another intracorporeal tissue such as a digestive tract and the like are separated from each other. As a result, the anchor member and the locking member can be independently mounted to the target intracorporeal tissue, respectively. The mounting of the anchor member to the intracorporeal tissue such as an abdominal wall or chest wall can be easily carried out by following the method of tying-up the anchor member of the present invention.

Since the anchor member and the locking member can be detachably connected by the first connection portion and the second connection portion that can be detachably connected by a magnetic force and the like, if the holding apparatus is to be re-mounted at another spot or a different type of locking member is required, it is only necessary that the first connection portion and the second connection portion are separated from each other, another type of the locking member is carried in, and connected by the magnetic force and the like again, and there is no need to remove the anchor member having been mounted to the intracorporeal tissue.

By using the medical holding means of the present invention, there is no interrupting of a field of view of an endoscope or a treatment site by the intracorporeal tissue other than a target to be treated, the treatment can be conducted rapidly and accurately, and the entire operation time can be reduced.

BRIEF DESCRIPTION OF THE DRAWINGS

FIG. 1 a diagram illustrating an example of an anchor member of a medical holding apparatus of the present invention.

FIG. 2 a diagram illustrating another example of an anchor member of a medical holding apparatus of the present invention.

FIG. 3 a diagram illustrating another example of an anchor member of a medical holding apparatus of the present invention.

FIG. 4 a diagram illustrating another example of an anchor member of a medical holding apparatus of the present invention.

FIG. 5 a diagram illustrating another example of an anchor member of a medical holding apparatus of the present invention.

FIG. 6 a diagram illustrating another example of an anchor member of a medical holding apparatus of the present invention.

FIG. 7 a diagram illustrating an example of a locking member of a medical holding apparatus of the present invention.

FIG. 8 a diagram illustrating another example of a locking member of a medical holding apparatus of the present invention.

FIG. 9 a diagram illustrating another example of a locking member of a medical holding apparatus of the present invention.

FIG. 10 a diagram illustrating an example of an anchor-member tying-up assisting tool for assisting tying-up of the anchor member shown in FIG. 1.

FIG. 11 a diagram illustrating an example of an anchor-member tying-up assisting tool for assisting tying-up of the anchor member shown in FIG. 4.

FIG. 12 a diagram illustrating an example of an anchor-member tying-up assisting tool for assisting tying-up of the anchor member shown in FIG. 3.

FIG. 13 a diagram illustrating an example of a state where an intracorporeal tissue is held in a body cavity using the medical holding apparatus of the present invention.

FIG. 14 a diagram illustrating an example of a state where the anchor member is tied up to a body wall, and the locking member is detachably connected to the anchor member.

FIG. 15 a diagram illustrating an example of a state where the anchor member is tied up to a body wall, and the locking member is detachably connected to the anchor member.

FIG. 16 a diagram illustrating an arrangement example of magnets of a first connection portion and a second connection portion.

FIG. 17 a diagram illustrating an inside structure of the first connection portion of the anchor member shown in FIG. 5.

FIG. 18 a diagram illustrating a structure of the tying-up portion of the anchor member shown in FIG. 5.

FIG. 19 a diagram illustrating movement of a magnet and a magnetic force line in the first connection portion of the anchor member shown in FIG. 5.

FIG. 20 a diagram illustrating a structure of the tying-up portion of the anchor member shown in FIG. 6.

FIG. 21 a diagram illustrating a structure in another mode of the tying-up portion of the anchor member shown in FIG. 6.

FIG. 22 a diagram illustrating an example of a state where an intracorporeal tissue such as a stomach or intestine is held in a body cavity using the medical holding apparatus of the present invention.

FIG. 23 a diagram illustrating another example of a anchor member of a medical holding apparatus of the present invention.

FIG. 24 a diagram of the first connection portion of an embodiment of the anchor member seen from a distal end side.

FIG. 25 a diagram illustrating another example of a locking member of a medical holding apparatus of the present invention.

FIG. 26 (*a*) is a diagram illustrating a form when a locking member is introduced into a body cavity. (*b*) is a diagram illustrating a state where the locking member is separated in the body cavity and the holding portion is expanded.

FIG. 27 a diagram illustrating an example of a state where a plurality of the locking members in FIG. 9(*b*) are connected to the single anchor member so as to hold the intracorporeal tissue.

FIG. 28 a diagram illustrating an example of a state where uterine adnexas are held in a body cavity using the medical holding apparatus of the present invention.

FIG. 29 a diagram illustrating an example of a state where a lung is held through a chest wall using the medical holding apparatus of the present invention.

FIG. 30 a diagram illustrating an example of a state where a lung is held using the medical holding apparatus of the present invention and an affected part is ablated.

EXPLANATION OF SYMBOLS 2, 12, 22, 32, 62, 72, 73: anchor member
3, 13, 23*a* 23*b*, 33: locking member
4, 14, 24, 34, 64, 74, 76: tying-up portion (puncture needle)
5, 15, 25, 35, 65, 75, 77: first connection portion
71: rod-like body
78A, 78B, 78C: inner cylinder
79: magnet
80: outer shell
42, 52, 82*a*, 82*b*: holding portion
41, 51, 81*a*, 81*b*, 51*a*, 51*b*, 51*c*, 51*d*: second connection portion
44: mesh
6, 16, 26: anchor-member tying-up assisting tool
10: body wall
A: stomach
B: colon
FOU: fundus uteri
Ov: ovaria
Ly: lymphaden
BL: broad ligament
S: automatic dissection/suturation tool for lung ablation
Lu: lung
AT: trachea
EP: thoracoscope (endoscope)
HpLy: hilar lymph node

BEST MODE FOR CARRYING OUT THE INVENTION

A preferred embodiment of a medical holding apparatus, an anchor-member tying-up assisting tool for tying it up and a method of tying-up, and a method of using the medical holding apparatus in the present invention will be described below in detail referring to the attached drawings.

FIGS. 1 to 6 and FIG. 23 are diagrams illustrating examples of an anchor member of the medical holding apparatus of the present invention. FIGS. 7 to 9 and FIGS. 25 to 26 are diagrams illustrating examples of a locking member of the medical holding apparatus of the present invention.

The medical holding apparatus is provided with the anchor member 2, 12, 22, 32, 62, 72 or 73 and the locking member 3, 13, 23a, 23b, in FIGS. 25(a) to 25(h) and FIG. 26(a) (or 26(b)). These anchor members and locking members can be combined arbitrarily. A plurality of the locking members may be combined with the single anchor member (See FIG. 27).
(Anchor Member)

The anchor member has a tying-up portion to be tied up to an intracorporeal tissue and a first connection portion. A structure of the tying-up portion is not particularly limited as long as it can mount the anchor member to the intracorporeal tissue so as to be rendered immovable. For example, tying-up portion 4 or 34 having a spiral puncture needle (FIG. 1 or 4), the tying-up portion 24 having a hook-like puncture needle (FIG. 3) or the tying-up portion 14 having a straight puncture needle (FIG. 2) can be mentioned, and a clip provided with opposing claws, a ring or a band made of an elastic material that can reduce an opening diameter so as to tie the intracorporeal tissue, a sucker for sucking the organ or tissue by a negative pressure and the like can be further mentioned. Considering a tying-up strength and the like, the tying-up portion having a puncture needle is preferable.
(Embodiment 1 of Anchor Member)

The anchor member 2 shown in FIG. 1 comprises the tying-up portion 4 having a spiral puncture needle and a first connection portion 5 on which a spiral convexo-concave is engraved on an outer circumferential face. The anchor member 2 can be screwed with the intracorporeal tissue by screwing the spiral puncture needle of the tying-up portion 4 into the intracorporeal tissue.

As an assisting tool for screwing, an anchor-portion tying-up assisting tool 6 as shown in FIG. 10 can be exemplified. This anchor-member tying-up assisting tool 6 comprises a cylindrical member 7 and a pushing member 8.

The cylindrical member 7 has a lumen into which the anchor member 2 can be inserted so that the tying-up portion is oriented to a distal end side and the first connection portion to a proximal end side. On an inner circumferential face of the cylindrical member 7, a spiral convexo-concave corresponding to the spiral convexo-concave engraved on the outer circumferential face of the first connection portion 5 is engraved. The pushing member 8 pushes the inserted anchor member from the rear from the cylindrical member proximal end side (right end in FIG. 10). When the anchor member 2 is pushed from the rear by the pushing member 8, the anchor member 2 advances while rotating by the screwing between the spiral convexo-concaves on the anchor-member outer circumferential face and on the inner circumferential face of the cylindrical member 7 (advances to the left side in FIG. 10) and is projected out of the cylindrical-member distal end (left end in FIG. 10) while the anchor member 2 is rotating. An angle of the spiral convexo-concaves engraved on the outer circumferential face of the anchor member 2 and on the inner circumferential face of the cylindrical member 7 with respect to the axial direction can be selected as appropriate to an angle with which a parallel motion of the pushing member 8 is converted to a rotary motion of the anchor member 2.
(Embodiment 2 of Anchor Member)

FIG. 4 shows another anchor member 32. This anchor member 32 comprises a tying-up portion 34 having a spiral puncture needle and a columnar first connection portion 35. The anchor member 32 can be screwed with the intracorporeal tissue by screwing the spiral puncture needle of the tying-up portion 34 into the intracorporeal tissue.

As an assisting tool for screwing, an anchor-portion tying-up assisting tool 16 as shown in FIG. 11 can be exemplified. This anchor-member tying-up assisting tool 16 comprises a cylindrical member 17 and a pushing member 18. The pushing member 18 is composed of a portion 18A for pushing the first connection portion of the anchor member 32, a rod-like member 18B having a spiral convexo-concave engraved on an outer circumferential face connected to a proximal end side of the portion, and a cylindrical member 18C having an inner circumferential shape to be screwed together the convexo-concave engraved on the rod-like member. The portion 18A for pushing the first connection portion is rotatable around an axis of the cylindrical member 17 but is fixed so as not to move in the axial direction.

And the portion 18A for pushing the first connection portion and the rod-like member 18B are fastened so as to rotate in an interlocking manner. The cylindrical member 18C is screwed so that the rod-like member 18B becomes rotatable and when the cylindrical member 18 is moved in the axial direction, the rod-like member 18B is rotated, and the portion 18A for pushing the first connection portion is rotated by the rotation. The torque of the portion 18A for pushing the first connection portion is transmitted to the anchor member 32 in contact therewith, the anchor member 32 is rotated, and the spiral puncture needle is screwed into the intracorporeal tissue. The angle of the spiral convexo-concaves engraved on the outer circumferential face of the rod-like member 18B and the inner circumferential face of the cylindrical member 18C with respect to the axial direction can be selected as appropriate so that the parallel motion of the cylindrical member is converted to the rotary motion of the rod-like member.

As another assisting tool for screwing the anchor member provided with the tying-up portion having the spiral puncture needle, for example, such a tool can be exemplified that a spiral groove or rib (rail) is provided on the inner circumferential face of the cylindrical member 17, a spiral groove or rib is provided on the outer circumferential face of the pushing member on the distal end side (portion corresponding to the portion 18A for pushing the first connection portion in FIG. 11), and the assisting tool is rotated by fitting in the spiral rail while the pushing means advances in the axial direction at the same time.

Alternatively, the proximal end side of the pushing means may be simply pushed while being rotated manually. A lever or a grip portion such as a handle and the like can be provided on the proximal end side of the pushing member in order to facilitate twisting and rotation of the pushing member.

In order to transmit the rotary motion of the pushing means to the anchor member without waste, such a structure can be realized by detachably coupling a distal end of the pushing means to the first connection portion of the anchor member by a magnetic force, a planar fastener, convexo-concave fitting and the like so that the anchor member is also rotated when the pushing means is rotated.

By using such anchor-member tying-up assisting tool, the anchor member can be easily tied up to the intracorporeal tissue. Specifically, a method can be proposed that the anchor member composed of the tying-up portion to be tied up to the intracorporeal tissue and the first connection portion is inserted into a lumen of the cylindrical member so that the tying-up portion is oriented to the distal end side and the first connection portion to the proximal end side; the cylindrical member distal end is brought close to a predetermined intracorporeal tissue surface; and the anchor member is pushed from the cylindrical member proximal end side so as to project the anchor member out of the cylindrical member distal end and to tie up the anchor member to the intracorporeal tissue.

(Embodiment 3 of Anchor Member)

FIG. 3 shows an anchor member 22 composed of a tying-up portion 24 having a hook-like puncture needle and a columnar first connection portion 25. By hooking the hook-like puncture needle of the tying-up portion 24 on the intracorporeal tissue for hooking, the anchor member can be fixed to the intracorporeal tissue.

The hook-like puncture needle preferably has elasticity. In the case of the anchor member provided with the tying-up portion having the hook-like puncture needle with elasticity, as shown in FIG. 12(a), the hook-like puncture needle can be extended substantially straight in the longitudinal direction of the cylindrical member, when the anchor member is inserted into a cylindrical member 27. And the inserted anchor member is pushed by a pushing member 28 from the cylindrical member proximal end side, and the anchor member is projected out of the cylindrical member distal end. As shown in FIGS. 12(b) and 12(c), when the anchor member is projected out of the distal end of the cylindrical member, the hook-like puncture needle having been extended straight in the longitudinal direction is released from restraining by the cylindrical member and recovered to an original hook-like shape. If the puncture needle distal end has been attached to the intracorporeal tissue at the recovery, the puncture needle can puncture and hook the intracorporeal tissue. As mentioned above, the anchor member can be easily tied up to the intracorporeal tissue. The puncture needle with elasticity can be made of an elastic body such as metal or a super elastic body such as shape memory alloy.

(Embodiment 4 of Anchor Member)

FIG. 2 shows an anchor member 12 composed of a tying-up portion 14 having a straight puncture needle and a columnar first connection portion 15. The anchor member 12 can be tied up by penetrating the puncture needle to outside the body from the body cavity side and by restraining the penetrated straight puncture needle outside the body using latching means 9.

The straight puncture needle preferably has a length exceeding a thickness of a body wall. As a result, the straight puncture needle inserted from the body cavity side as shown in FIG. 15 penetrates a body wall 10 such as an abdominal wall or chest wall, and the distal end of the needle is exposed outside the body. By restraining the exposed needle by the latching means 9 such as a clip, ring and the like so as not to be removed, the anchor member 12 can be tied up to the intracorporeal tissue 10.

The latching means 9 may be provided as a separate member such as a clip and the like as above or a mechanism that can expand a diameter of the needle distal end portion after penetration into the abdominal wall, chest wall and the like may be incorporated in the straight puncture needle. The mechanism to expand the diameter, for example, includes a balloon inflated by injecting a gas; a mechanism in which a lumen is provided at the distal end of the puncture needle, an expansive material such as rubber foam is made small and packed in the lumen, which is suppressed by a cap plug and the like, and after the needle is penetrated, the plug is removed so that the expansive material is expanded; and the like.

A position of the puncture needle restrained by the latching means 9 is not particularly limited. By adjusting a penetrating length of the puncture needle and by offsetting a position restrained by the latching means, a distance between the anchor member 12 remaining in the body cavity and the body wall can be arbitrarily adjusted. The tying-up portion 14 having this straight puncture needle can be pulled out of the intracorporeal tissue simply by removing the latching means. Since the tying-up portion 14 having the straight puncture needle does not have to be rotated or twisted as the tying-up portion having the above spiral puncture needle or hook-like puncture needle in order to be removed, removal after completion of the treatment is easier than them.

A material, length, thickness and the like of the puncture needles composing the tying-up portion are not particularly limited as long as the object of the present invention is satisfied, but it is preferably covered by a biocompatible material. The biocompatible materials include a resin such as silicone, Teflon (registered trademark) and the like, for example. When the anchor member is delivered to a desired spot in a body cavity or the anchor member is removed from the intracorporeal tissue and taken out of the body, if it is carried out in a state inserted in the cylindrical member of the anchor-member tying-up assisting tool as above, trouble such that the tying-up portion (puncture needle) of the anchor member and the like touches and damages another organ or tissue and the like can be prevented.

(Embodiment 5 of Anchor Member)

FIG. 5 shows an anchor member 62 composed of a tying-up portion 64 having a straight puncture needle and a columnar first connection portion 65. Its appearance is the same as the anchor member 12 shown in FIG. 2 and the anchor member can be tied up by penetrating the puncture needle 64 to outside the body from the body cavity side and by restraining the penetrated straight puncture needle using the latching means outside the body.

The anchor member 62 comprises a lumen having the first connection portion 65 and the tying-up portion 64 communicate with each other. And a needle distal end portion 64A, a shaft 64B and a magnet portion 65A fastened to each other are contained in the lumen that can rotate with the longitudinal direction as the center axis. At the magnet portion 65A, as shown in FIG. 17, small-sized magnets 65D are aligned along the circumference. When the needle distal end portion 64A is rotated, the magnet portion 65A is rotated through the shaft 64B. At the anchor member 62 shown in FIG. 5, a hole through which a rod-like member 64C can be penetrated is provided at the needle distal end portion 64A (FIG. 18). As shown in FIG. 18(a), the rod-like member 64C is penetrated through the hole, and as shown in FIG. 18(b), the needle distal end portion 64A can be easily rotated using the rod-like member 64C as a lever FIG. 19 is a diagram enlarging the inside of the first connection portion and a diagram illustrating a state where the small-sized magnets 65D are moved by rotation of the magnet portion, by which a magnetic force line is changed.

As shown in FIGS. 5 and 19, the first connection portion 65 is made of a material not transmitting the magnetic force line such as a diamagnetic substance such as copper and the like, and at a connection surface 65C, holes 65B communicating with the lumen of the first connection portion are provided. The holes 65B are provided with substantially the same interval as an arrangement interval of the small-sized magnets 65D in the above-mentioned magnet portion 65A. As shown in FIG. 19(a), when the magnet portion 65A is rotated and the small-sized magnets 65D are brought to positions corresponding to the holes 65B, the magnetic force line exits to the outside through the holes 65D and can magnetically attract the second connection portion and firmly connect them. And as shown in FIG. 19(b), when the magnet portion 65A is further rotated and the small-sized magnets 65D are brought to the positions not corresponding to the holes 65B, the magnetic force line is cancelled by the diamagnetic substance, the magnetic attracting force with the second connection portion is weakened, and the connection can be easily released. The sizes and the interval of the small-sized magnets 65D and the holes 65B are not particularly limited as long as the magnetic force can be controlled as above in the positional relation between the small-sized magnets 65D and the holes 65B.

(Embodiment 6 of Anchor Member)

FIG. 6 shows an anchor member 72 composed of a tying-up portion 74 having a straight puncture needle and a columnar first connection portion 75. The appearance is the same as that of the anchor member 12 in Embodiment 4, and the anchor member can be tied up by penetrating the puncture needle 74 to outside the body from the body cavity side and by restraining the penetrated straight puncture needle using the latching means outside the body.

The anchor member 72 comprises a lumen having the first connection portion 75 and the tying-up portion 74 communicate with each other, and a needle distal end portion 74A, conductive lines 74B1 and 74B2, and an electromagnet 75A are contained in the lumen.

The conductive lines 74B1 and 74B2 are electrically connected to the electromagnet 75A, and when a direct-current electricity is passed through the conductive lines, magnetism is generated at the electromagnet 75A, which strongly attracts the second connection portion made of a ferromagnetic substance, permanent magnet and the like and can connect it to the first connection portion. When the current is cut off, the magnetism in the electromagnet 75A is lost, the attracting force of the second connection portion is gone, and the connection can be easily released. Alternatively, by having a current in an opposite direction flow, the S-N poles are reversed, the second connection portion made of a permanent magnet is repelled, and release of the connection is made possible.

The needle distal end portion 74A has, as shown in FIG. 20, a distal end portion 74A1 and a distal end portion 74A2 electrically insulated and physically integrated. And the conductive line 74B1 is electrically connected to the distal end portion 74A1 and the conductive line 74B2 to the distal end portion 74A2. By connecting a terminal of an external power supply to each of the distal end portion 74A1 and the distal end portion 74A2, an electric current can flow to the electromagnet from the needle distal end portion 74A through the conductive lines.

A method of supplying an electric current to the electromagnet is not limited to the method shown in FIG. 20 but, for example, a needle distal end portion 74A3 is constructed detachable from the cylindrical member of the tying-up portion 74, and when the external power supply is to be connected to the electromagnet, the needle distal end portion 74A3 is removed, and the conductive lines may be pulled out of the lumen of the tying-up portion 74 and connected to the terminal of the external power supply (FIG. 21). Alternatively, a battery is incorporated in the lumen of the needle distal end portion 74A, the first connection portion 75 and the like, a switch is provided at the needle distal end portion 74A and the like, the current supply from the incorporated battery to the electromagnet is controlled by on/off of the switch so that the electromagnet can be turned on/off.

(Embodiment 7 of Anchor Member)

FIG. 23 shows an anchor member 73 composed of a tying-up portion 76 having a straight puncture needle and a columnar first connection portion 77. The appearance is the same as that of the anchor member 12 in Embodiment 4, and the anchor member can be tied up by penetrating the puncture needle 76 to outside the body from the body cavity side and by restraining the penetrated straight puncture needle using the latching means outside the body.

In the anchor member 73, the first connection portion has a cavity inside and the tying-up portion is cylindrical having a lumen. The cavity of the first connection portion and the cylindrical lumen of the tying-up portion communicate with each other.

In the columnar cavity of the first connection portion, a columnar magnet 79 is provided movably in the longitudinal direction. The magnet is preferably a permanent magnet such as a rare-earth magnet. An outer shell 80 of the first connection portion is made of a non-magnetic substance such as titanium.

In Embodiment 7, the columnar magnet is contained movably in the longitudinal direction in an inner cylinder 78 (78A, 78B, 78C). The inner cylinder has stoppers at its both ends so that the columnar permanent magnet does not project from the both ends of the inner cylinder. The inner cylinder 78 is formed by connecting two cylinders 78A and 78C made of a highly magnetically permeable material such as permalloy through a ring 78B made of a non-magnetic body such as brass by brazing and the like. The inner cylinder is movable in the longitudinal direction in the outer shell of the first connection portion. The non-magnetic ring is provided at such a position that when the permanent magnet is located at the most proximal end side of the inner cylinder, it is on the distal end side farther from the distal end of the permanent magnet, while when the permanent magnet is located on the most distal end side of the inner cylinder, it is located in the middle of the permanent magnet.

At the proximal end of the permanent magnet 79, a rod-like body 71 penetrating the cylinder lumen of the typing-up portion and movable in the longitudinal direction is linked so that the rod-like body and the magnet can move in the longitudinal direction in an interlocking manner. The proximal end of the rod-like body projects from the proximal end of the cylinder lumen of the tying-up portion so that it can be picked with hands and the like.

By picking the proximal end of the rod-like body so as to move the rod-like body in the longitudinal direction, the magnet is moved in the longitudinal direction in the cavity of the first connection portion. If the rod-like body is pushed into the most distal end side, the permanent magnet and the inner cylinder are located at the most distal end of the outer shell. When the permanent magnet is brought to the most distal end position of the outer shell (FIG. 23(*a*)), the magnetic force line from the permanent magnet leaks outside from the distal end face of the outer shell, and when the second connection portion is brought close to the distal end of the outer shell, it is attracted by the magnetic force and the first connection portion and the second connection portion are connected to each other.

When the rod-like body is pulled to the proximal end side, first, the permanent magnet is moved to the proximal end side in the inner cylinder and comes to the stopper at the most proximal end of the inner cylinder. And the inner cylinder and the permanent magnet are moved together in the outer shell to the proximal end side and come to the most proximal end of the outer shell. When the permanent magnet is located at the most proximal end of the outer shell (FIG. 23(*b*)), the magnetic force line from the permanent magnet is interrupted by the non-magnetic ring and also separated from the distal end of the outer shell, and the magnetic force to attract the second connection portion is weakened, and the connection between the first connection portion and the second connection portion is released.

(Locking Member)

The locking member is composed of the second connection portion. The second connection portion can be detachably connected to the above-mentioned first connection portion directly or with another intracorporeal tissue held between the first connection portion and the second connection portion.

By sandwiching another intracorporeal tissue between the first connection portion and the second connection portion, the intracorporeal tissue can be held. As the intracorporeal tissues that can be sandwiched between the first connection portion and the second connection portion, a membrane such as board ligament of the uterus, mesenterium (tunica vasculosa to small intestine), mesocolon (tunica vasculosa to colon), greater omentum (membrane attached to stomach), small omentum (membrane attached to stomach), margin of hepar, and gall bladder itself and the like are mentioned. By sandwiching a membrane around an organ or tissue between the first connection portion and the second connection portion without directly holding the organ or tissue in the body cavity and the like, the organ or tissue in the body cavity can be held (See FIG. 28).

The above-mentioned locking member may be further provided with a medical operation portion, or a holding portion for holding another intracorporeal tissue, a medical instrument or a drug.

A structure of the holding portion is not particularly limited as long as another intracorporeal tissue, a medical instrument or a drug can be held. For example, the holding portion may have a bag, a basket, a thread, a wire and the like that can hold another intracorporeal tissue, a medical instrument or a drug. Other holding portions include a clip provided with opposing claws, a portion that can sandwich an intracorporeal tissue by throttling the clip by a ring (See FIG. 9), a ring or a band made of an elastic material that can reduce an opening diameter and tie the intracorporeal tissue, a sucker for sucking the organ or tissue by a negative pressure, a bag that can wrap the organ or tissue, a mesh, a basket and the like.

Also, the holding portions may be provided with a through hole 42 through which a wire rod 43 such as a string, a wire or a rod as shown in FIG. 7.

The holding portion shown in FIG. 8 is composed of a loop wire 52 and a ring 53 that can tie and throttle the wire. Another intracorporeal tissue, a medical instrument or a drug is contained in a space formed between the wire 52, and by moving the ring 53 to the left side in FIG. 8 so as to narrow the space formed between the wire 52, another intracorporeal tissue and the like can be held.

A holding portion 23*a* or 23*b* shown in FIG. 9 is composed of a clip 82*a* or 82*b* made of an elastic body that is hardly damaged when an organ or tissue is sandwiched and a ring 83*a* or 83*b* movable in the length direction of the clip, and when the ring 83*a* or 83*b* is moved to the left side in the figure, an interval between the clip distal ends is narrowed so that the organ or tissue and the like can be sandwiched. Drop preventing means is provided at the clip 82*a* or 82*b* so that the ring 83*a* or 83*b* does not drop into the body cavity.

A projection 84 is provided as the drop preventing means in FIG. 9(*a*), while the clip 82*b* itself is larger than an inner diameter of the ring in FIG. 9(*b*), but they are not limiting as long as they are provided with a mechanism to prevent drop. The clip 82*a* or 82*b* and the second connection portion 81*a* or 81*b* are connected to each other by a wire rod such as a wire, a rod and the like so that the clip 82*a* or 82*b* can move flexibly.

The locking member may be transformed as shown in FIG. 26. FIG. 26(*a*) shows a form when being introduced into a body cavity. FIG. 26(*b*) shows a form where the locking member is transformed in the body cavity so as to extend the holding portion composed of a mesh made of a biocompatible material. When it is introduced into the body cavity, by making it compact as shown in FIG. 26(*a*), introduction time can be reduced. After introduction into the body cavity, second connection portions 51*a*, 51*b*, 51*c* and 51*d* are separated so as to extend the holding portion as shown in FIG. 26(*b*) so that even a large intracorporeal tissue can be held. The separated second connection portions 51*a*, 51*b*, 51*c* and 51*d* can be connected to a plurality of anchor members, respectively, or can be collected and connected to a single anchor member similarly to FIG. 27.

By these holding portions, digestive tracts such as colon, small intestine, stomach and the like, uterine adnexas such as fundus uteri, broad ligament, ovaria, oviduct, uterine cervix and the like, and organs such as lung, heart and the like which are easily moved in a body cavity can be held. Also, another medical instrument or a drug can be safely locked in the body cavity such as an abdominal cavity or chest cavity.

The locking member and the anchor member may be connected in one-to-one correspondence but as shown in FIG. 27, a plurality of locking members may be connected to the single anchor member.

The medical operation portion is a portion having the same function as a medical instrument used in an operation. The medical operation portions include an image pickup device such as CCD camera, an illumination device such as LED (light-emitting diode), forceps, scissors, a scalpel (including electric scalpel), a snare, laser and the like. They can be provided singularly or in combination of two or more.

FIG. 25 is a diagram illustrating an example of the locking member provided with the medical operation portion. The locking member shown in FIG. 25 is composed of the columnar second connection portion and the medical operation portion attached to the distal end side of the second connection portion.

FIG. 25(*a*) or 25(*b*) shows that scissors are attached at the distal end of the locking member. FIG. 25(*c*) or 25(*d*) shows that forceps are attached at the distal end of the locking member. FIG. 25(*a*) or 25(*c*) shows an open state of the scissors or forceps, while FIG. 25(*b*) or 25(*d*) shows a closed state of the scissors or forceps. Inside the cylinder (second connection portion) of the locking member in FIG. 25 is provided with a mechanism for opening/closing the scissors or forceps. The opening/closing mechanism is not particularly limited but an electric circuit which is turned ON/OFF by a magnetic switch or optical switch and the like can be mentioned, for example.

FIG. 25(*e*) shows that a monopolar electric scalpel is attached at the distal end of the locking member. FIG. 25(*f*) shows that a bipolar electric scalpel is attached at the distal end of the locking member. FIG. 25(*g*) shows that laser light can be irradiated from the distal end of the locking member so that an operation on a diseased part can be conducted by laser. Alternatively, instead of the laser beam, an illumination function may be provided by attaching a light-emitting device such as LED. Moreover, FIG. 25(*h*) shows that a CCD camera is provided at the locking member so that inside the body cavity can be observed. The CCD camera and the light emitting device may be provided in combination. Inside each locking member, a mechanism for supplying power to devices such as electric scalpel, laser, LED, CCD camera and the like is provided. The mechanism for supplying power is not particularly limited but a mechanism includes a power supply, a switch such as a magnetic switch, an optical switch and the like, electric device for adjusting a voltage and the like, for example.

(First Connection Portion and Second Connection Portion)

The first connection portion and the second connection portion composing each of the anchor member and the locking member are constructed so that they can be detachably connected. For the detachable connection, a sucker for sucking by a negative pressure, a plane fastener, convexo-concave fitting that can be locked by rotation, a magnetic force and the like can be used, for example, and the magnetic force is preferably used.

Specific examples using the magnetic force include those in which the first connection portion and the second connection portion are made of a paramagnetic substance or a ferromagnetic substance, preferably of the ferromagnetic substance, and at least one of the first connection portion and the second connection portion is a magnet (permanent magnet or electromagnet).

The paramagnetic substances include aluminum and the like. As the ferromagnetic substance, iron, iron alloy, cobalt, nickel and the like are preferably used. As the magnet, samarium-cobalt alloy ($Sm_2Co_{17}+X$ and the like), neodymium-iron alloy ($Nd_2Fe_{14}B$ and the like), alnico alloy ($Ni_{14}CO_{24}Al_8Cu_3+Fe$ and the like), ferrite magnet ($BaO$ $6Fe_2O_3$, $SrO$ $6Fe_2O_3$ and the like) are preferably used.

And by bringing the first connection portion and the second connection portion close to each other, both are attracted to each other and connected by the magnetic force. Since they are connected only by the magnetic force, both can be separated from each other by separating the first connection portion and the second connection portion to outside the range where the magnetic force can reach.

If the first connection portion and the second connection portion are connected by a strong magnetic force, it is sometimes difficult to separate them easily. In order to facilitate the separation, the N-pole and the S-pole of the magnetic substance on the face where the first connection portion and the second connection portion are in contact with each other may be arranged alternately along the circumference as shown in FIG. 16, for example. Usually, the S-pole and the N-pole of the first connection portion 5 and the N-pole and the S-pole of the second connection portion 41 at the positions corresponding to them are attracted and connected to each other. By twisting the first connection portion 5 and the second connection portion 41, the correspondence between the N-pole and the S-pole becomes correspondence of N-pole and N-pole or S-pole and S-pole, by which the both are repelled by each other and the first connection portion 5 and the second connection portion 41 can be easily separated. Also, as mentioned above, by having the structure as in FIG. 5 or 6, separation of the connection is facilitated. Moreover, as shown in FIG. 23, by making the magnet in the first connection portion movable in the longitudinal direction, the separation of the connection can be facilitated by adjustment of the magnetic force.

FIG. 24 is a diagram of the first connection portion of an embodiment of the anchor member seen from the distal end side. A region 9 in FIG. 24 is made of a non-magnetic substance such as plastic so as not to transmit the magnetic force line, and regions 7 and 8 are made of metal and the like so that the magnetic force line can be transmitted easily. Behind the region 7 and the region 8, independent magnets are arranged and magnetically insulated by the region 9. The magnetic polarity and magnetic force of the magnets behind the region 7 and the region 8 can be independently changed. For example, if an electromagnet is used, the magnetic force can be changed by an electric current. By preparing the first connection portion with the above structure and the second connection portion provided with a mechanism operated by the magnetism (a magnetic switch, for example) at portions corresponding to the region 7 and the region 8, connection/separation between the first connection portion and the second connection portion can be controlled by adjustment of the magnetic force transmitted through the region 7, and an operation of the medical operation portion and the like can be controlled by turning on/off the circuit inside the cylinder (second connection portion) of the above-mentioned locking member by adjustment of the magnetic force transmitted through the region 8, for example.

In the example shown in FIG. 24, by preparing the first connection portion in which the region 8 is replaced by a material transmitting light such as an infrared light and the like and a light-emitting device such as an optical fiber, LED and the like is installed behind it, and the second connection portion in which a light-receiving device such as an optical switch is installed at a portion corresponding to the region 8, the connection/separation between the first connection portion and the second connection portion can be controlled by the magnetic force transmitted through the region 7, and the operation of the medical operation portion and the like can be controlled by turning on/off the circuit inside the second connection portion of the above-mentioned locking member by optical communication by the infrared light and the like in the region 8, for example.

In FIG. 24, only one region 8 is shown, but there is no limitation in providing a plurality of regions equivalent to the region 8. Also, the shape and arrangement of the region 7 or the region 8 is not limited to those in FIG. 24, either.

The connection surface between the first connection portion and the second connection portion is usually a plane, but in order to prevent displacement of the connection surface, the mutual connection surfaces of the first connection portion and the second connection portion may be in the convexo-concave shape that fits. The connection surface that fits is not particularly limited by the shape. The shapes include a projecting spherical face and a recessed spherical face, a projecting cone and a recessed cone, convexo-concave in the chrysanthemum petal state and the like, for example.

The medical holding apparatus of the present invention is used in an operation in a body cavity such as an abdominal cavity and chest cavity, and it is preferably made of a biocompatible material or covered by the biocompatible material. The biocompatible materials include a resin such as silicon, Teflon (registered trademark) and the like, for example.

As mentioned above, with regard to the medical holding apparatus of the present invention, first, using the means as shown in FIGS. 10 to 12 and the like, for example, the anchor member composed of the tying-up portion to be tied up to the intracorporeal tissue and the first connection portion is inserted into the lumen of the cylindrical member so that the tying-up portion is oriented to the distal end side and the first connection portion to the proximal end side; the cylindrical member distal end is brought close to the predetermined intracorporeal tissue surface; the anchor member is pushed from the cylindrical member proximal end side so as to project the anchor member out of the cylindrical member distal end and to tie up the anchor member to the intracorporeal tissue; and as shown in FIG. 13, 22 or 28 to 30, for example, another intracorporeal tissue, a medical instrument or a drug is held by the holding portion of the locking member composed of the holding portion and the second connection portion, and the second connection portion can be connected to the first connection portion by the magnetic force and the like. As mentioned above, the intracorporeal tissue other than the treatment target can be shunted outside the range of the field of view of the endoscope or a treatment site easily, by which the treatment can be conducted rapidly and accurately, and the entire operation time can be reduced.

FIG. 22 is a diagram illustrating a state where the anchor member 12 shown in FIG. 2 and the locking member 23a shown in FIG. 9 grasp a digestive tract such as stomach, colon and the like. The anchor member and the locking member are detachably connected by the magnetic force and the like as mentioned above. The straight puncture needle of the anchor member penetrates the body wall. By moving the straight puncture needle up and down outside the body, the first connection portion of the anchor member is moved up and down. With that motion, the second connection portion of the locking member and the clip-like holding portion are moved vertically, by which the digestive tract such as stomach and colon grasped by the holding portion can be moved up and down. As a result, by shunting the digestive tract and the like from the operation treatment site and the operation of the treatment site can be conducted easily.

Since the anchor member and the locking member can be easily connected or separated by the detachable first connection portion and the second connection portion, if the locking member is re-mounted at another spot, it is only necessary to separate the second connection portion from the first connection portion and to re-connect it to a first connection portion of another anchor member tied up at another spot, and if the locking member of a different type or with a different function is required, it is only necessary that another type of locking member is carried in and re-connected to the anchor member, and there is no need to remove the anchor member attached to the intracorporeal tissue. If the locking member having the medical operation portion is connected, treatment of a diseased area can be conducted by the medical operation portion. As in FIG. 22, by operating an end of the straight puncture needle of the anchor member outside the body, the position of the locking member having the medical operation portion connected by the first connection portion and the second connection portion can be changed.

FIG. 28 is a diagram illustrating an example of a state where uterine adnexa is held in the body cavity using the medical holding apparatus of the present invention. For example, the entire uterus is lifted up and a lymph node Ly is treated in a uterine cancer lymph node dissection. In FIG. 28, in order to lift up the entire uterus, the anchor member 73 shown in FIG. 23 is penetrated into the body wall from inside the body cavity and attached to the body wall. And a broad ligament BL is held by attaching the first connection portion 77 of the anchor member 73 to the broad ligament BL, bringing the locking member 33 (shown by a dotted line in FIG. 28) close from the back side of the broad ligament, and connecting the first connection portion and the second connection portion by the magnetic force with the broad ligament held between them. By operating the tying-up portion of the anchor member projecting outside the body, the entire uterus can be lifted up.

FIG. 29 is a diagram illustrating an example of a state where a lung Lu is held through the chest wall using the medical holding apparatus of the present invention. In hilar lymph node dissection, for example, a lymph node HPLy located beside bronchus hidden behind the lung is treated. For the treatment, it is necessary to release air in the lung to flatten the lung and to turn down the lung so that the lymph node hidden behind the lung can be observed by a thoracoscope EP. In FIG. 29, the lung is picked by the holding portion of the locking member 23, the second connection portion of the locking member 23 is connected to the first connection portion of the anchor member 73 penetrated through the body wall from inside the body cavity and attached to the body wall, and the lung is lifted up. By operating the tying-up portion of the anchor member projecting outside the body in an arrow h so as to move the locking member 23, the lung can be turned down (the state where an upper part of the lung is turned down is shown by a dotted line).

FIG. 30 is a diagram illustrating an example of a state where the lung is held using the medical holding apparatus of the present invention and a diseased part is ablated. Pneumonectomy is usually conducted using an automatic dissection/suture tool S for pneumonectomy. In order to facilitate an operation by the automatic dissection/suture tool S for pneumonectomy, it is necessary to hold the lung. In FIG. 30, the lung is picked by the locking member 23, the locking member 23 is connected to the anchor member 73, the tying-up portion of the anchor member 73 projecting outside the body is operated so as to lift up the lung. By lifting up the lung in this way, dissection can be easily conducted only by lightly touching the lung with a blade of the automatic dissection/suture tool S for pneumonectomy.

As mentioned above, the medical holding apparatus of the present invention can easily shunt the intracorporeal tissue such as organs like heart, lung, digestive tract (stomach, small intestine, colon), hepar, gall bladder, uterine adnexas, bladder and the like interrupting the field of view in an endoscopic operation and the like, and time required for operation can be drastically reduced. Also, by lifting the intracorporeal tissue up using the medical holding apparatus of the present invention and by lightly touching the intracorporeal tissue with a blade of a dissection tool such as a scalpel, the intracorporeal tissue is easily incised from the touched portion. The medical holding apparatus of the present invention does execution particularly in lymphadenectomy, ablation of digestive tract and the like.

The invention claimed is:

1. A medical holding apparatus comprising:
an anchor member having a tying-up portion configured to puncture and be tied up to an intracorporeal tissue and a first connection portion; and
a locking member having a second connection portion,
in which the first connection portion and the second connection portion can be detachably connected by magnetic force to each other directly or with another intracorporeal tissue between the first connection portion and the second connection portion.

2. The medical holding apparatus according to claim 1, in which the tying-up portion has a spiral, hook-like or straight puncture needle that can be tied up by puncturing an intracorporeal tissue.

3. The medical holding apparatus according to claim 1, in which the tying-up portion has a straight puncture needle that can be tied up by penetrating an intracorporeal tissue; and
a latching means for restraining the straight puncture needle penetrating the intracorporeal tissue so that the first connection portion is positioned at a predetermined position is further comprised.

4. The medical holding apparatus according to claim 1, in which the first connection portion and/or the second connection portion is made of a paramagnetic substance or a ferromagnetic substance; and
at least any one of the first connection portion and/or the second connection portion is a magnet.

5. The medical holding apparatus according to claim 1, in which the anchor member and/or the locking member is covered by a biocompatible material.

6. The method of using the medical holding apparatus according to claim 1,
in which the anchor member is tied up to the intracorporeal tissue and the first connection portion of the anchor member is connected to the second connection portion of the locking member.

7. The method of using the medical holding apparatus according to claim 1,
in which the anchor member is tied up to the intracorporeal tissue and the first connection portion is connected to the second connection portion so that another intracorporeal tissue is sandwiched between the first connection portion of the anchor member and the second connection portion of the locking member.

8. The method of using the medical holding apparatus according to claim 1, comprising steps of:
inserting the anchor member having the tying-up portion to be tied up to an intracorporeal tissue and the first connection portion into a lumen of a cylindrical member so that the tying-up portion is oriented to a distal end side and the first connection portion to a proximal end side;
bringing the cylindrical member distal end close to a predetermined intracorporeal tissue surface;
pushing the anchor member from the cylindrical member proximal end side so as to project the anchor member out of the cylindrical member distal end and to tie up the anchor member to the intracorporeal tissue; and
connecting the second connection portion of the locking member to the first connection portion of the anchor member.

9. A medical holding apparatus comprising:
an anchor member having a tying-up portion configured to be tied to an intracorporeal tissue and a first connection portion; and
a locking member having a medical operation portion and a second connection portion,
in which the first connection portion and the second connection portion can be detachably connected by magnetic force, wherein the medical operation portion includes at least one medical instrument selected from the group consisting of an image pickup device, an illumination element, forceps, scissors, a scalpel, a snare, and laser.

10. The medical holding apparatus according to claim 9,
in which the tying-up portion has a straight puncture needle that can be tied up by penetrating an intracorporeal tissue; and
a latching means for restraining the straight puncture needle penetrating the intracorporeal tissue so that the first connection portion is positioned at a predetermined position is further comprised.

11. The medical holding apparatus according to claim 9,
in which the first connection portion and/or the second connection portion is made of a paramagnetic substance or a ferromagnetic substance; and
at least any one of the first connection portion and/or the second connection portion is a magnet.

12. A medical holding apparatus comprising:
an anchor member having a tying-up portion to be tied to an intracorporeal tissue and a first connection portion; and
a locking member having a holding portion for holding another intracorporeal tissue, a medical instrument or a drug and a second connection portion,
in which the first connection portion and the second connection portion can be detachably connected by magnetic force, wherein the holding portion has a bag, a basket, a thread, a wire, or a clip that can hold another intracorporeal tissue.

13. The medical holding apparatus according to claim 12,
in which the tying-up portion has a straight puncture needle that can be tied up by penetrating an intracorporeal tissue; and
a latching means for restraining the straight puncture needle penetrating the intracorporeal tissue so that the first connection portion is positioned at a predetermined position is further comprised.

14. The medical holding apparatus according to claim 12,
in which the first connection portion and/or the second connection portion is made of a paramagnetic substance or a ferromagnetic substance; and
at least any one of the first connection portion and/or the second connection portion is a magnet.

15. A medical anchor member comprising:
a tying-up portion to be tied up at an intracorporeal tissue; and
a first connection portion which can be detachably connected by magnetic force to another member which is external to the medical anchor member, wherein a tying up portion has a straight puncture needle that can be tied up by penetrating an intracorporeal tissue, and a latching means for restraining the straight puncture needle penetrating the intracorporeal tissue so that the first connection portion is positioned at a predetermined position is further comprised.

16. The medical anchor member according to claim 15,
in which the first connection portion has a cavity inside, the tying-up portion is cylindrical, the cavity of the first connection portion and an in-cylinder lumen of the tying-up portion communicate with each other;
a magnet movable in the longitudinal direction is provided in the cavity of the first connection portion;
a rod-like body penetrating the in-cylinder lumen of the tying-up portion and movable in the longitudinal direction is linked at a proximal end of the magnet; and
the rod-like body and the magnet are made movable in the longitudinal direction in an interlocking manner.

17. An anchor-member tying-up assisting tool comprising:
a cylindrical member having a lumen into which an anchor member having a tying-up portion to be tied up to an intracorporeal tissue and a first connection portion can be inserted so that the tying-up portion is oriented to a distal end side and the first connection portion to a proximal end side, wherein the first connection portion is configured to be and magnetically connected to another member which is external to the anchor member; and
a pushing-out member for projecting the anchor member out of the cylindrical member distal end by pushing the inserted anchor member from the cylindrical member proximal end side.

18. A method of tying-up an anchor member to an intracorporeal tissue, comprising steps of:
inserting the anchor member having a tying-up portion to be tied up to an intracorporeal tissue and a first connection portion into a lumen of a cylindrical member so that a tying-up portion is oriented to a distal end side and the first connection portion to a proximal end side, wherein the first connection portion is configured to be detachably and magnetically connected to another member which is external to the anchor member;
bringing the cylindrical member distal end close to a predetermined intracorporeal tissue surface; and pushing the anchor member from the cylindrical member proximal end side so as to project the anchor member out of the cylindrical member distal end.

19. A medical holding apparatus comprising:

an anchor member having a tying-up portion to be tied up to an intracorporeal tissue and a first connection portion; and a locking member having a second connection portion, in which the first connection portion and the second connection portion can be detachably connected to each other directly or with another intracorporeal tissue between the first connection portion and the second connection portion;

in which the tying-up portion has a straight puncture needle that can be tied up by penetrating an intracorporeal tissue; and a latching means for restraining the straight puncture needle penetrating the intracorporeal tissue so that the first connection portion is positioned at a predetermined position is further comprised.

20. A medical anchor member comprising:

a tying-up portion to be tied up at an intracorporeal tissue; and a first connection portion, in which the tying-up portion has a straight puncture needle that can be tied up by penetrating an intracorporeal tissue; and a latching means for restraining the straight puncture needle penetrating the intracorporeal tissue so that the first connection portion is positioned at a predetermined position is further comprised.

21. The medical anchor member according to claim 20, in which the first connection portion has a cavity inside, the tying-up portion is cylindrical, the cavity of the first connection portion and an in-cylinder lumen of the tying-up portion communicate with each other;

a magnet movable in the longitudinal direction is provided in the cavity of the first connection portion;

a rod-like body penetrating the in-cylinder lumen of the tying-up portion and movable in the longitudinal direction is linked at a proximal end of the magnet; and the rod-like body and the magnet are made movable in the longitudinal direction in an interlocking manner.

22. A medical holding apparatus comprising:

an anchor member having a tying-up portion to be tied to an intracorporeal tissue and a first connection portion; and a locking member having a medical operation portion and a second connection portion;

in which the first connection portion and the second connection portion can be detachably connected, the tying-up portion has a straight puncture needle that can be tied up by penetrating an intracorporeal tissue; and a latching means for restraining the straight puncture needle penetrating the intracorporeal tissue so that the first connection portion is positioned at a predetermined position is further comprised.

23. A medical holding apparatus comprising:

an anchor member having a tying-up portion to be tied to an intracorporeal tissue and a first connection portion; and a locking member having a holding portion for holding another intracorporeal tissue, a medical instrument or a drug and a second connection portion, in which the first connection portion and the second connection portion can be detachably connected;

the tying-up portion has a straight puncture needle that can be tied up by penetrating an intracorporeal tissue; and a latching means for restraining the straight puncture needle penetrating the intracorporeal tissue so that the first connection portion is positioned at a predetermined position is further comprised.

* * * * *